United States Patent [19]

Schaap et al.

[11] Patent Number: 5,795,987

[45] Date of Patent: Aug. 18, 1998

[54] ALKENE INTERMEDIATES FOR PREPARING 1,2-DIOXETANE COMPOUNDS

[75] Inventors: Arthur P. Schaap; Louis J. Romano; Jaidev S. Goudar, all of Detroit, Mich.

[73] Assignee: Board of Governors of Wayne State University, Detroit, Mich.

[21] Appl. No.: 910,072

[22] Filed: Aug. 12, 1997

Related U.S. Application Data

[60] Division of Ser. No. 218,308, Mar. 25, 1994, which is a continuation-in-part of Ser. No. 289,837, Dec. 27, 1988, Pat. No. 5,616,729, which is a continuation-in-part of Ser. No. 887,139, Jul. 17, 1986, abandoned.

[51] Int. Cl.$^6$ ................... C07D 207/00; C07D 311/82; C07F 7/00
[52] U.S. Cl. ................... 548/528; 548/303.7; 548/406; 548/542; 549/223; 556/486; 568/732
[58] Field of Search .................. 549/223; 568/732; 556/486; 548/303.7, 406, 528, 542

[56] References Cited

U.S. PATENT DOCUMENTS 4,857,652  8/1989  Schaap et al. ................... 549/510

FOREIGN PATENT DOCUMENTS 1461877  1/1977  United Kingdom .

OTHER PUBLICATIONS

J.E. McMurry et al, J. Amer. Chem. Soc. 105, 1660 (1983).
J.E. McMurry, Chem. Rev., 89, 1513 (1989).
A.P. Schaap et al, Clin. Chem., 35, 1863 (1989).
H.R. Schroeder et al., Anal. Chem. 48, 1933 (1976).
H.R. Schroeder in Luminescent Immunoassays: Perspectives in Endocrinology and Clinical Chemistry, M. Serio and M. Pazzagli, Eds., Raven Press, New York, pp. 129–146 (1982).
M. Pazzagli et al., J. Steroid Biochem., 19, 407 (1983).
T.P. Whitehead et al., Nature, 305, 158 (1983).
G.H. Thorpe et al., Clin. Chem., 31, 1335 (1985).
I. Weeks et al., Clin. Chem., 29, 1474 (1983).
I. Weeks et al., Clin. Chem., 29, 1480 (1983).
L.J. Arnold, Jr., et al., Clin. Chem., 35, 1588 (1989).
J.C. Hummelen et al., Pure Appl. Chem., 59, 639 (1987).
J.C. Hummelene t al., "Thermochemiluminescent Immunoassays, "in Complementary Immunoassays.
W.P. Collins, Ed., Wiley & Sons, New York, p. 191 (1988).
H. Wynberg et at., "1,2–Dioxetanes as Chemiluminescent Probes and Labels" in Bioluminescence and Chemiluminescence, M.A. DeLuca, W.D. McElroy, Eds., Academic Press, New York, p. 687 (1981).
J.C. Hummelen et al., Methods in Enzymology 133, 531 (1986).
L.J. Kricka, Ligand–Binder Assays, Marcel Dekker, Inc. New York, 1985, pp. 15–51.
M.Z. Atassi, "Chemical Modification and Cleavage of Proteins," Chap. 1 in Immunochemistry of Proteins, vol. 1, Plenum Press, New York, 1977, pp. 1–161.
L.J. Kricka, Ligand–Binder Assays, Marcel Dekker, Inc. New York 1985, pp. 18–20, Table 2.2.
T.H. Ji, "Bifunctional Reagents," Methods in Enzymology, 91, 580–609 (1983).
R.M. Buckland, Nature, 320, 557–558 (1986).
T.W. Greene, Protective Groups in Organic Synthesis, John Wiley, New York, 198, pp. 10–72 (1981).
A.P. Schaap et al., Tetrahedron Lett., 935 1987.
A.P. Schaap et al., Tetrahedron Lett, 1155 1987.
A.P. Schaap et al, Tetrahedron Lett, 1159 1987.

Primary Examiner—Amelia Owens
Attorney, Agent, or Firm—Ian C. McLeod

[57] ABSTRACT

Dioxetanes which couple with organic and biological molecules of the formula:

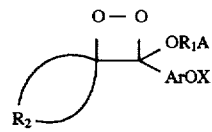

wherein X is a leaving group which is removed by an activating agent to produce light, wherein A is a coupling substituent, Ar is a substituent selected from the group consisting of phenyl and naphthyl to provide a label are described. $R_1$ is an optional linker substituent and can have between 1 and 30 carbon atoms with some of the carbon atoms being oxygen, sulfur, nitrogen or phosphorus. Ar as phenyl is preferred. The dioxetane coupled molecules are useful in assays of all types where luminescence can be used as an indicator.

19 Claims, 2 Drawing Sheets

- Dioxetane 1c
- Hydrolysis product
- Dioxetane-linked antibody

- Dioxetane 1c
- Dioxetane-linked antibody

Starting Reaction, Fraction 19, Fraction 20, Fraction 21

100 ng    10 ng    1 ng

ALKENE INTERMEDIATES FOR PREPARING 1,2-DIOXETANE COMPOUNDS

CROSS-REFERENCE TO RELATED APPLICATION

This application is a division of Ser. No. 218,308, filed Mar. 25, 1994, which is a continuation-in-part of U.S. application Ser. No. 07/289,837, filed Dec. 27, 1988, now U.S. Pat. No. 5,616,729, which is a continuation-in-part of Ser. No. 06/887,139, filed Jul. 17, 1986, now abandoned.

BACKGROUND OF THE INVENTION (1) Field of the Invention

The present invention relates to triggerable stable 1,2-dioxetanes which have the ability to bind to organic and biological molecules for use in assays and the like. In particular, the present invention relates to 1,2-dioxetanes which have an ability to react with biological materials without materially altering their essential function.

(2) Prior Art
1. Chemical Triggering of Stabilized 1,2-Dioxetanes

Thermally stable dioxetanes which can be triggered by chemical and enzymatic processes to generate chemiluminescence on demand have recently been discovered (A. P. Schaap, patent application Ser. No. 887,139, filed Jul. 17, 1986; A. P. Schaap, R. S. Handley, and B. P. Giri, *Tetrahedron Lett.*, 935 (1987); A. P. Schaap, T. S. Chen, R. S. Handley, R. DeSilva, and B. P. Giri, *Tetrahedron Lett.*, 1155 (1987); and A. P. Schaap, M. D. Sandison, and R. S. Handley, *Tetrahedron Lett.*, 1159 (1987)). To do this, new synthetic procedures to produce dioxetanes with several key features have been developed: (1) the stabilizing influence of spiro-fused adamantyl groups has been utilized to provide dioxetanes that have "shelf lives" of years at ambient temperature and (2) new methods for triggering the chemiluminescent decomposition of the stabilized dioxetanes have been developed.

The required alkenes have been prepared by reaction of adamantanone with aromatic esters of ketones using titanium trichloride/LAH in THF (A. P. Schaap, U.S. Pat. No. 4,857,652). This is the first report of the intermolecular condensation of ketones and esters to form vinyl ethers using these reaction conditions. Although McMurry had earlier investigated the intramolecular reaction of ketone and ester functional groups, cyclic ketones and not vinyl ethers were prepared by this method (J. E. McMurry and D. D. Miller, *J. Amer. Chem. Soc.*, 105, 1660 (1983) and J. E. McMurry, Chem. Rev., 89, 1513 (1989)).

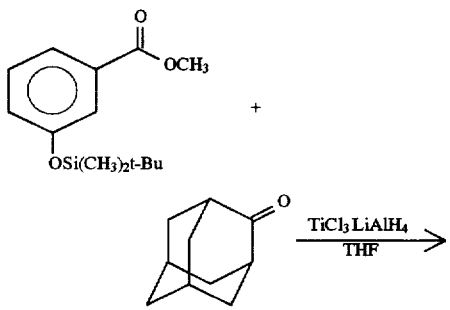

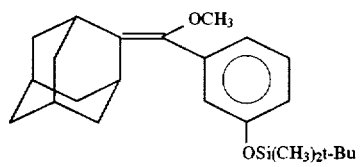

Photooxygenation of these vinyl ethers affords dioxetanes that are easily handled compounds with the desired thermal stability. For example, the dioxetane shown below exhibits an activation energy of 28.4 kcal/mol and a half-life at 25° C. of 3.8 years. Samples of this dioxetane in o-xylene have remained on the laboratory bench for several months with no detectable decomposition.

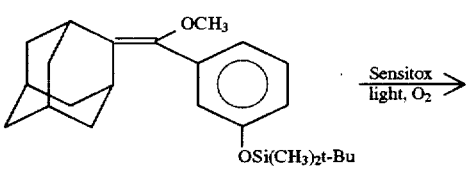

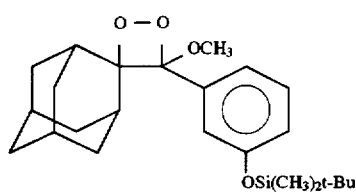

However, the chemiluminescent decomposition of this dioxetane can be conveniently triggered at room temperature by removal of the silyl protecting group with fluoride ion to generate the unstable, aryloxide form which cleaves to yield intense blue light. The half-life of the aryloxide-substituted dioxetane is 5 seconds at 25° C. The spectrum of the chemiluminescence in DMSO exhibits a maximum at 470 nm which is identical to the fluorescence of the anion of the ester cleavage product (methyl 3-hydroxybenzoate) and the fluorescence of the spent dioxetane solution under these conditions. No chemiluminescence derived from adamantanone fluorescence appears to be produced. The chemiluminescence quantum yield for the fluoride-triggered decomposition measured relative to the luminol standard was determined to be 0.25 (or a chemiluminescence efficiency of 25%). Correction for the fluorescence quantum yield of the ester under these conditions ($\phi_f$=0.44) gave an efficiency for the formation of the singlet excited ester of 57%, the highest singlet chemiexcitation efficiency yet reported for a dioxetane prepared in the laboratory.

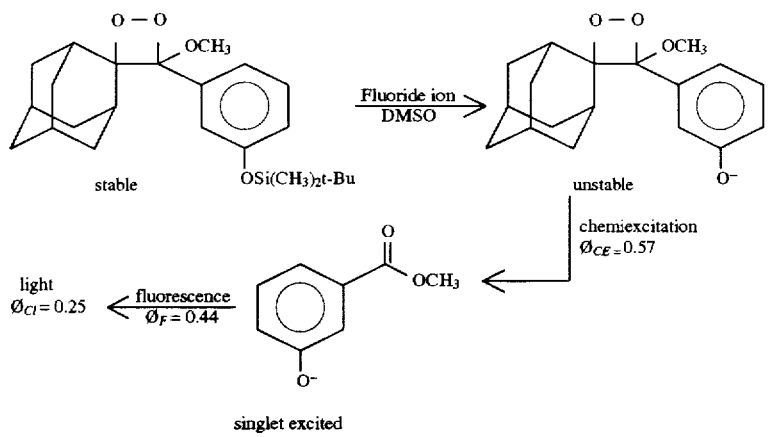

2. Enzymatic Triggering of Stabilized 1,2-Dioxetanes

Biological assays such as immunoassays and DNA hybridizations involving enzymes utilized a wide variety of substrates which either form a color (chromogenic) or become fluorescent (fluorogenic) upon reaction with the enzyme. As part of the investigation of triggering methods, the first dioxetanes which can function as chemiluminescent enzyme substrates have been discovered (A. P. Schaap, U.S. patent application Ser. No. 887,139; A. P. Schaap, R. S. Handley, and B. P. Giri, Tetrahedron Lett., 935 (1987); A. P. Schaap, T. S. Chen, R. S. Handley, R. DeSilva, and B. P. Giri, Tetrahedron Lett., 1155 (1987); A. P. Schaap, M. D. Sandison, and R. S. Handley, Tetrahedron Lett., 1159 (1897) and A. P. Schaap, Photochem. Photobiol., 47S, 50S (1988)). Use of these peroxides in biological systems requires dioxetanes which are thermally stable at the temperature of the enzymatic reaction and do not undergo rapid spontaneous decomposition in the aqueous buffers. The spiro-fused adamantyl dioxetanes described in the previous section meet these requirements. Dioxetanes have been prepared which can be enzymatically modified to generate the aryloxide form. Decomposition of this unstable intermediate provides the luminescence. Dioxetanes have been synthesized which can be triggered by various enzymes including aryl esterase, acetylcholinesterase, alkaline phosphatase and beta-galactosidase.

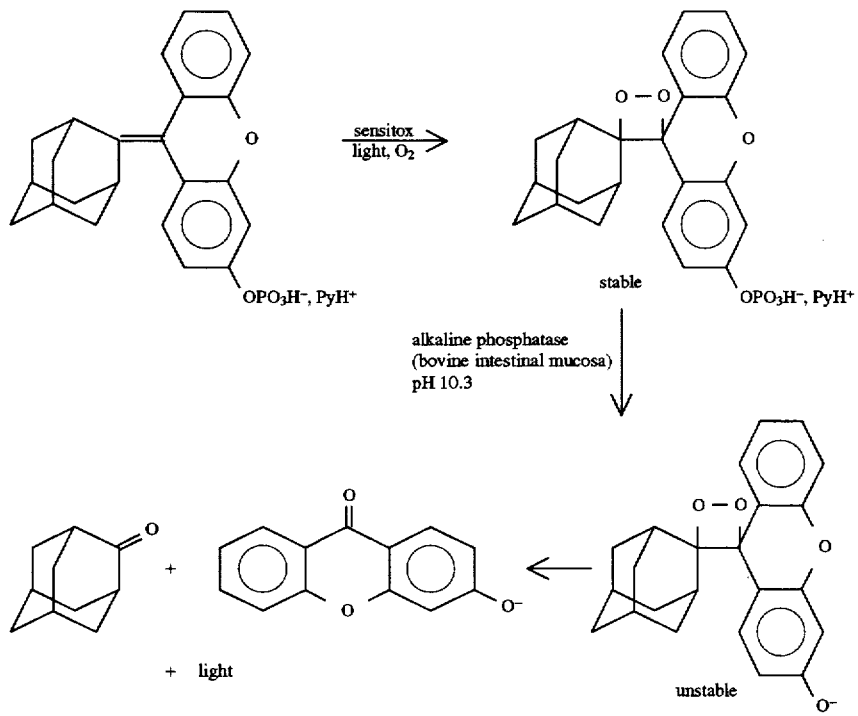

For example, enzymatic triggering by alkaline phosphatase has been observed with the phosphate-substituted dioxetane shown above derived from 3-hydroxy-9H-xanthen-9-one and adamantanone. The dioxetane is thermally stable with an activation energy of 30.7 kcal/mol and a half-life at 25° C. of 12 years. The dioxetane is not only stable in organic solvents but also shows very slow spontaneous decomposition in aqueous buffers. Triggering experiments were conducted using alkaline phosphatase from bovine intestinal mucosa and the phosphate-protected dioxetane at pH 10.3 in 0.75M 2-amino-2-methyl-1-propanol buffer. The total light emission was found to be linearly dependent on the dioxetane concentration. The rate of decay of the emission is a function of enzyme concentration while the total light emission is independent of the enzyme concentration. The chemiluminescence spectrum for the phosphatase-catalyzed decomposition was obtained at room temperature in the buffer solution. A comparison of this chemiluminescence spectrum with the fluorescence spectrum of the spent reaction mixture and the fluorescence spectrum of the hydroxyxanthone cleavage product in the buffer indicates that the emission is initiated by the enzymatic cleavage of the phosphate group from the dioxetane to yield the unstable aryloxide dioxetane which generates the singlet excited anion of hydroxyxanthone.

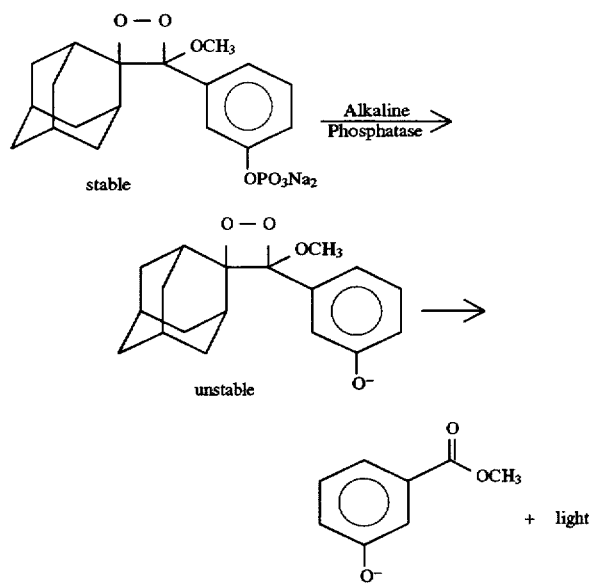

Phosphatase triggering experiments have also been conducted using the phosphate-protected dioxetane shown above derived from methyl 3-hydroxybenzoate and adamantanone with alkaline phosphatase at pH 9.6 in 0.75M 2-amino-2-methyl-1-propanol buffer. Addition of the enzyme to a $10^{-4}$M solution of dioxetane results in chemiluminescence emitted over several minutes. As a result of the very low background luminescence from slow hydrolysis of the dioxetane in the buffer, less than $10^{-18}$ mol (1 attomol) of alkaline phosphatase can be detected in the presence of enhancers (A. P. Schaap, H. Akhavan and L. J. Romano, *Clin. Chem.*, 35, 1863 (1989) and A. P. Schaap, U.S. patent applications Ser. Nos. 07/224,681 and 07/317, 585).

3. Chemiluminescent Direct Labels for Biological Assays (a) Luminol and isoluminol. The aminophthalhydrazides, luminol and isoluminol react with $H_2O_2$ and a peroxidase enzyme catalyst under basic conditions with emission of light. The reaction is also catalyzed by small amounts of several metal ions including Fe(III), Cu(II) and Cr(III). The first chemiluminescent immunoassay using luminol as a label was reported by Schroeder for an assay of biotin. (H. R. Schroeder, P. O. Vogelhut, R. J. Carrico, R. C. Boguslaski, R. T. Buckler, *Anal. Chem.* 48, 1933 (1976)). Several applications of the use of luminol derivatives as labels have been reported since then (H. R. Schroeder in *Luminescent Immunoassays: Perspectives in Endocrinology and Clinical Chemistry*, M. Serio and M. Pazzagli, Eds., Raven Press, New York, pp 129–146 (1982); M. Pazzagli, G. Messeri, A. L. Caldini, G. Monetti, G. Martinazzo and M. Serio, *J. Steroid Biochem.*, 19, 407 (1983); *Bioluminescence and Chemiluminescence New Perspectives*, J. Scholmerich, et al., Eds., J. Wiley & Sons, Chichester (1987)). Various enhancers have also been employed in conjunction with the use of luminol to increase the intensity of light emitted. These include D-luciferin (T. P. Whitehead, G. H. Thorpe, T. J. Carter, C. Groucutt and L. J. Kricka, *Nature*, 305, 158 (1983)) and p-iodophenol (G. H. Thorpe, L. J. Kricka, S. B. Mosely and T. P. Whitehead *Clin. Chem.*, 31, 1335 (1985)).

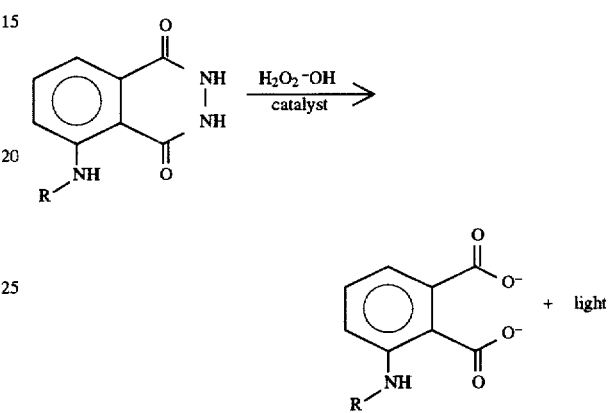

(b) Acridinium and phenanthridinium esters. Aromatic esters of N-methyl acridinium and phenanthridinium carboxylic acid undergo a chemiluminescent reaction upon treatment with $H_2O_2$ and a base. The stability of these esters decreases markedly at high pH. Incorporation of a linker group R on the aromatic moiety as shown below allows attachment of the chemiluminescent label to antigens, antibodies or solid supports. This work has been reported in a patent (F. McCapra, D. E. Tutt, R. M. Topping, British Patent No. 1,461,877 (1977)) and in the following papers (I. Weeks, I. Beheshti, F. McCapra, A. K. Campbell, J. S. Woodhead, *Clin. Chem.*, 29, 1474 (1983); I. Weeks, A. K. Campbell, J. S. Woodhead, *Clin. Chem.*, 29, 1480 (1983)). These compounds are used as labels in commercial immunoassay kits for the detection of TSH (LumaTag™; London Diagnostics, Inc..; Eden Prairie, Minn.) and free thyroxin (Magic Lite System; Ciba-Corning Diagnostics Corp.; Medfield, Mass.). This technology has also been used to label DNA probes (L. J. Arnold, Jr., P. W. Hammond, W. A. Wiese, N. C. Nelson, *Clin. Chem.*, 35, 1588 (1989)).

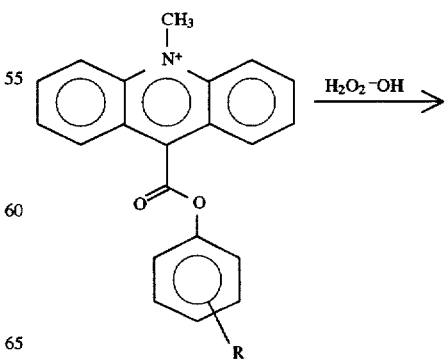

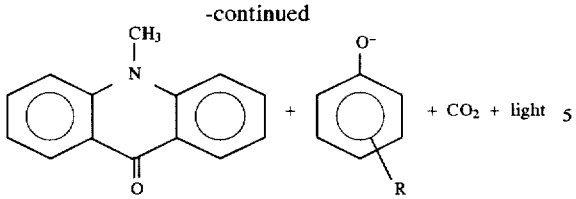 + $CO_2$ + light (c) Adamantylideneadamantane dioxetanes for thermochemiluminescent detection. Derivatives of adamantylideneadamantane dioxetane have been prepared by Wynberg and co-workers for the direct labeling of antibodies and proteins. (J. C. Hummelen, T. M. Luider, H. Wynberg, *Pure Appl. Chem.*, 59, 639 (1987); J. C. Hummelen, T. M. Luider, H. Wynberg, "Thermochemiluminescent Immunoassays", in *Complementary Immunoassays*, W. P. Collins, Ed., Wiley and Sons, New York, p. 191 (1988); H. Wynberg, E. W. Meijer, J. C. Hummelen, "1,2-Dioxetanes as Chemiluminescent Probes and Labels" in *Bioluminescence and Chemiluminescence*, M. A. DeLuca, W. D. McElroy, Eds., Academic Press, New York, p. 687 (1981)). Detection of chemiluminescence requires that the labeled analyte be immobilized on a plastic disk and heated to 250° to 300° C. These extreme temperatures are incompatible with the development of a homogeneous immunoassay system which is performed in aqueous solution. Since the chemiluminescence quantum yield from the thermolysis of adamantylideneadamantane dioxetane is quite low ($\phi_{CL}=10^{-4}$) the technique of energy transfer to a highly fluorescent acceptor must be employed to achieve higher sensitivity of detection. This requires that a second label, a fluorescer, also be chemically attached either to the analyte or to the first label (J. C. Hummelen, T. M. Luider, H. Wynberg, *Methods in Enzymology*, 133, 531 (1986)). Reaction R groups which were used to chemically bind the dioxetane to proteins included those shown below.

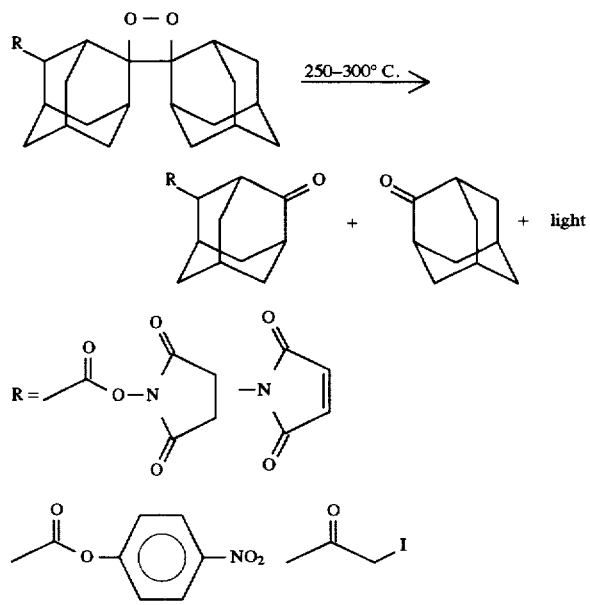

4. Labeling Procedures

A wide variety of procedures for chemically binding labels to organic and biological molecules are described in the literature (see, for example: L. J. Kricka, *Ligand-Binder Assays*, Marcel Dekker, Inc., New York, 1985, pp. 15–51 and M. Z. Atassi, "Chemical Modification and Cleavage of Proteins," Chapter 1 in *Immunochemistry of Proteins*, Vol. 1, Plenum Press, New York, 1977, pp. 1–161, and references therein). Antibodies and proteins are conveniently labeled by reaction of certain nucleophilic groups present in proteins (—SH, —OH, —NH$_2$, —COOH) with labels bearing chemically reactive groups such as those shown below in Table 1. Appropriately functionalized nucleic acids and DNA probes can also be labeled by synthesizing amine or thiol-containing nucleic acids and reacting these molecules with the corresponding reactive group on the dioxetane. Alternatively, nucleic acids (primarily oligonucleotides) can be linked to dioxetanes by the reaction of a hydroxyl with an activated phosphoramidite. In this case the phosphoramidite could be positioned on the nucleic acid and the hydroxyl placed on the dioxetane or vice versa. Other types of molecules which can be labeled include enzymes, protein antigens, haptens, steroids, carbohydrates, fatty acids, prostaglandins, thromboxanes, leukotrienes, nucleosides and nucleotides.

TABLE 1

Reactive Groups for Chemical Binding of Labels to Organic and Biological Molecules 1) Groups which are reactive towards amines (—NH$_2$).

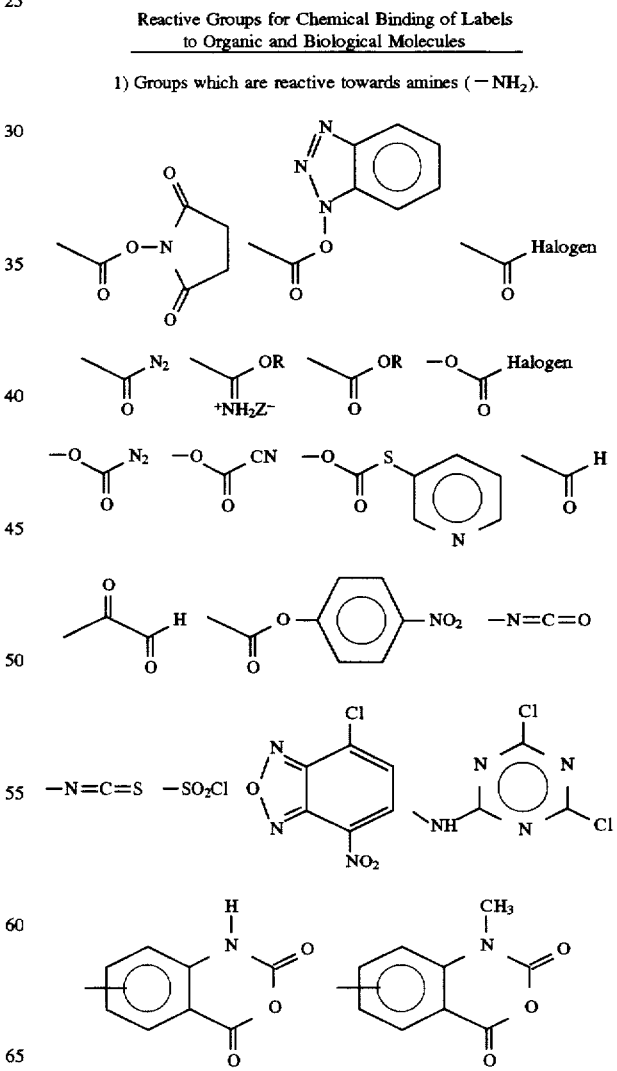

TABLE 1-continued

Reactive Groups for Chemical Binding of Labels to Organic and Biological Molecules 2) Groups which are reactive towards thiols (—SH).

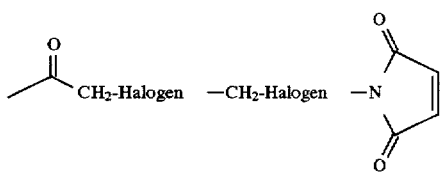

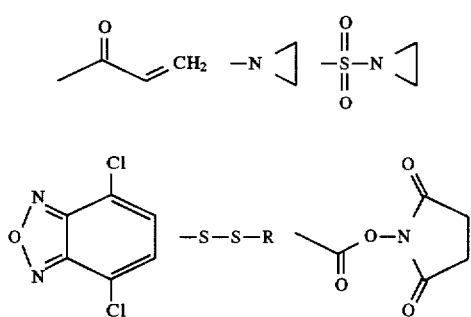

3) Groups which are reactive towards carboxylic acids (—CO$_2$H).

Bifunctional coupling reagents may also be used to couple labels to organic and biological molecules with moderately reactive groups (see L. J. Kricka, *Ligand-Binder Assays*, Marcel Dekker, Inc., New York, 1985, pp. 18–20, Table 2.2 and T. H. Ji, "Bifunctional Reagents," *Methods in Enzymology*, 91, 580–609 (1983)). There are two types of bifunctional reagents, those which become incorporated into the final structure and those which do not and serve only to couple the two reactants. Fluorescein can be used to form a complex with anti-fluorescein. Additionally, psoralen can be used to covalently bind to DNA.

Physical binding or complex formation of a chemiluminescent dioxetane to a molecule of interest may be accomplished as shown below by chemical bonding of the label to a molecule of biotin (vitamin H) and chemical bonding of the organic or biological molecule of interest to either avidin or streptavidin. The latter two compounds are bacterial proteins with four high-affinity binding sites for biotin (R. M. Buckland, *Nature*, 320, 557–558 (1986) and references therein).

Detection of an Organic or Biological Molecule (Antigen) Through Labeled Biotin or Labeled Avidin or Streptavidin

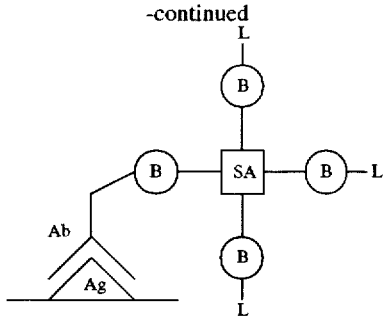

Ag, antigen; Ab, antibody; B, biotin; SA, streptavidin; L, label

OBJECTS

It is therefore an object of the present invention to provide a method and chemiluminescent triggerable 1,2-dioxetanes for use in detecting organic and biological materials and compounds. Further, it is an object of the present invention to provide a method and chemiluminescent triggerable 1,2-dioxetanes which can be used in immunoassays and DNA hybridization assays.

IN THE DRAWINGS

GENERAL DESCRIPTION

Figure 1:
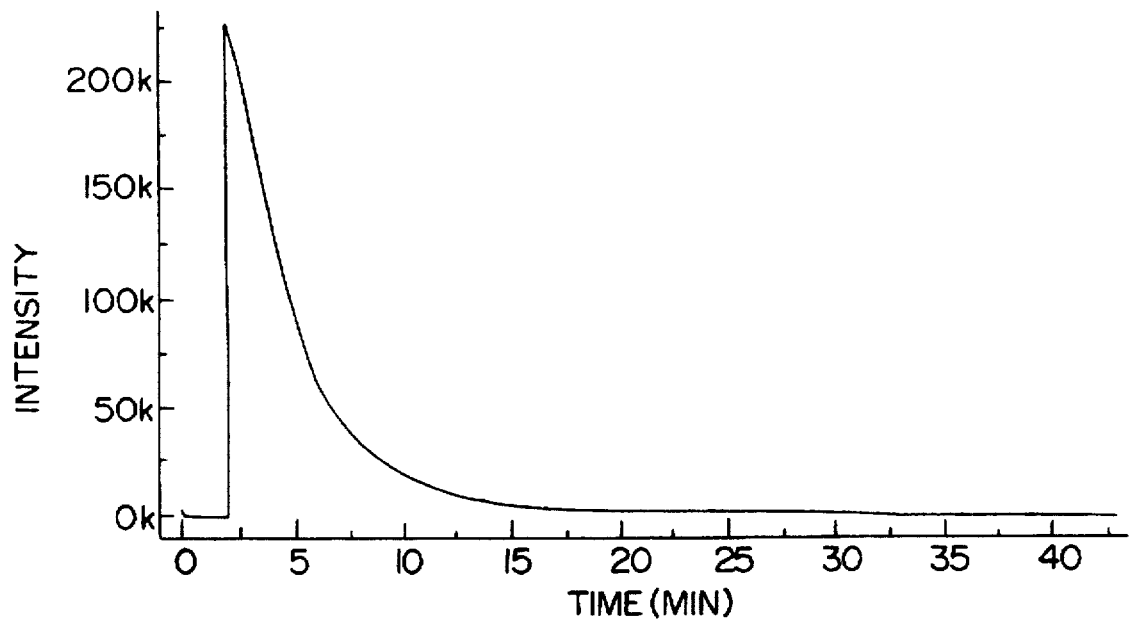
FIG. 1 is a graph of intensity versus time for bovine serum (BSA) albumin labeled with dioxetane 1a described hereinafter when triggered with sodium hydroxide.

The present invention relates to a dioxetane compound of the formula:

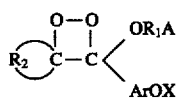

wherein Ar is an aromatic substituent selected from the group consisting of phenyl and naphthyl, wherein A is selected from the group consisting of a substituent which chemically couples with an organic or biological molecule and a substituent which physically couples to a biomolecule to provide the dioxetane compound as a label on the molecule, wherein $R_1$ is optional and when present is a linking substituent containing 1 to 30 carbon atoms and optionally hetero atoms selected from the group consisting of oxygen, nitrogen, sulfur and phosphorus substituted for some of the carbon atoms, wherein X is a chemically labile substitutent which is removed by an activating agent so that light is produced by the dioxetane and wherein

is a polycyclic alkylene substituent containing 6 to 30 carbon atoms.

The present invention also relates to an alkene compound of the following formula used to produce the above 1,2-dioxetane compound:

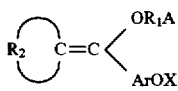

wherein A is a substituent selected from the group consisting of a substituent which chemically couples with an organic or biological molecule and a substituent which physically couples with a biomolecule to provide the dioxetane compound as a label on the molecule, wherein $R_1$ is optional and when present is a linking substituent containing 1 to 30 carbon atoms and optionally heteroatoms selected from the group consisting of oxygen, nitrogen, sulfur, phosphorus substituted for some of the carbon atoms, wherein X is a chemical labile group which is removed by an activating agent so that light is produced by the 1,2-dioxetane produced from the alkene compound and

a polycyclic alkene group containing 6 to 30 carbon atoms. The

substituent is preferably adamantyl. Other polycyclic alkylene substituents containing 6 to 30 carbon atoms can be used.

The $R_1$ substituent is preferably

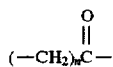

wherein n is an integer between 1 and 30; or

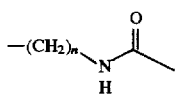

wherein n is an integer between 1 and 30 or —$(CH_2)_n$ wherein n is between 1 and 30.

Ar is selected from the group consisting of phenyl and naphthyl. Phenyl is preferred.

A is preferably an n-hydroxysuccinimide group, a carboxylic acid group, a hydroxyl group, biotin, an antibody reactive molecule where the antibody binds or reacts with the molecule to provide a label for the antibody, maleimide, amine and the like. Numerous such chemically reactive or coupling groups can function as A as previously described. Where A is biotin a preferred molecule is

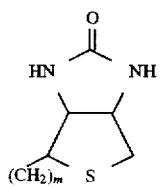

wherein m is an integer between 2 and 30.

The present invention involves chemically triggerable, stable 1,2-dioxetanes which can be bound to organic and biological molecules by chemical bonds and additionally in some cases through physical interactions. Removal of the X group by an activating agent generates an unstable aryloxide dioxetane which decomposes spontaneously to produce light. The intensity of the resulting chemiluminescence provides a direct measure of the quantity of labeled organic or biological molecule. Several examples of dioxetane labels are shown with specific reactive groups A and leaving groups X. Various groups $R_1$ serve as linker arms between the oxygen atom attached to the dioxetane and the reactive group A.

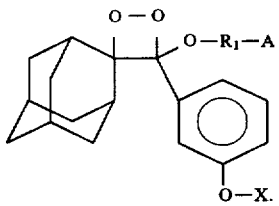

$R_1$ can be comprised of carbon and heteroatoms such as oxygen, nitrogen, sulfur and phosphorus with chain lengths of 1 to 30 atoms. Further, rings containing carbon and heteroatoms can be used as part of the linker arm. Alternatively, A can be attached directly to the oxygen atom without a linker arm. Possible reactive groups A include N-hydroxysuccinimide, maleimide, iodoacetate, phosphoramidite, isocyanate, isothiocyanate, hydroxyl, sulfhydryl, amino, carboxyl and others shown in Table 1. Possible X groups include any chemical leaving group which is stable during the process of combining the reactive group A with the organic or biological molecule. Subsequent treatment of the labeled molecule bearing the group X with the appropriate activating agent produces chemiluminescence. The examples shown herein and the U.S. patent application Ser. No. 887,139, filed Jul. 17, 1986 illustrate typical X groups which can be removed chemically as well as enzymatically. The corresponding X-oxy groups include but are not limited to hydroxyl, alkyl or aryl carboxyl ester, inorganic oxyacid salt, alkyl or aryl silyloxy and oxygen-pyranoside. Additional examples of X groups which can be removed to trigger the chemiluminescence are found in the standard treatises on protecting groups (T. W. Greene, *Protective Groups in Organic Synthesis*, John Wiley, New York, 198, pp. 10–72) (1981)). Such groups are $Si(CH_3)_2tBu$, $SiPh_2tBu$, $CH_2OCH_2CH_2Si(CH_3)_3$, $CH_2CH_2Si(CH_3)_3$ and $Si(CH_2CH_3)_2i$—Pr. Additionally, it should be noted that other aryl groups such as naphthyl can be used in place of meta-phenyl. Examples of -ArOX with naphthyl include

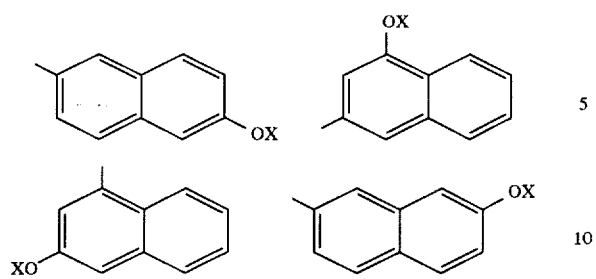

SPECIFIC DESCRIPTION

Synthesis of 1,2-Dioxetane Compounds

Dioxetanes are prepared by photooxygenation of the corresponding alkenes using procedures described herein. Alternatively, one reactive group A in a dioxetane can be exchanged for another group A by means of chemical reactions such as in the conversion of dioxetanes 1 to the corresponding dioxetanes 2. Dioxetanes 3a-c are prepared by photooxygenation of alkenes 14, 17 and 20.

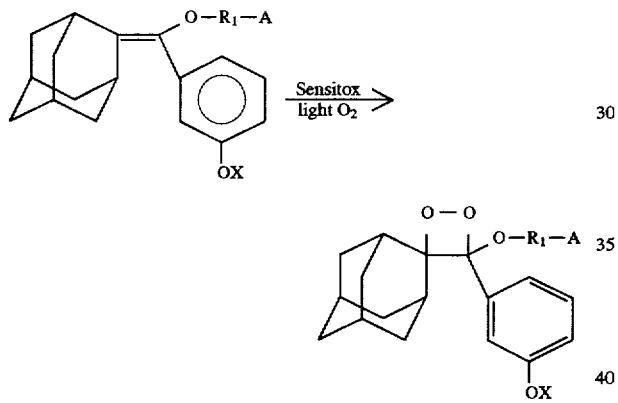

Dioxetane Synthesized

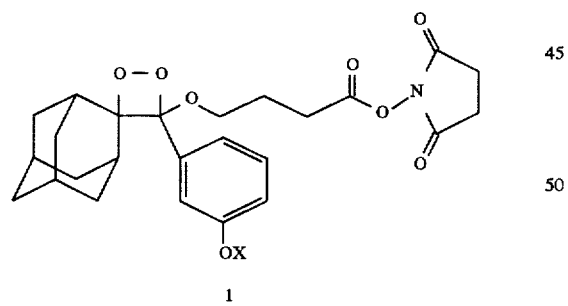

1

(a) X = H
(b) X = Si(CH$_3$)$_2$t-Bu
(c) X = Si(Ph$_2$t-Bu

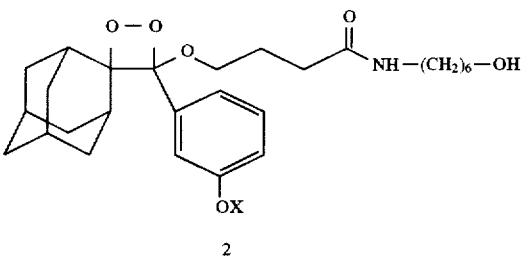

2

(a) X = Si(CH$_3$)$_2$t-Bu
(b) X = Si(Ph$_2$t-Bu

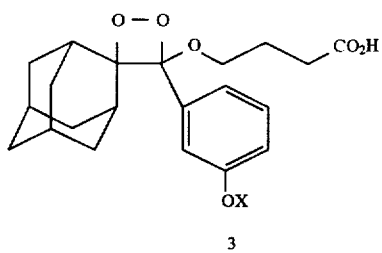

3

(a) X = H
(b) X = Si(CH$_3$)$_2$t-Bu
(c) X = Si(Ph$_2$t-Bu

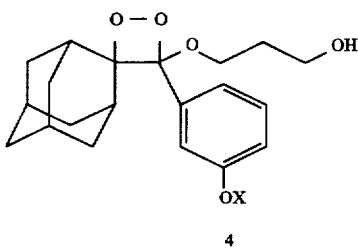

4

(a) X = Si(Ph$_2$t-Bu

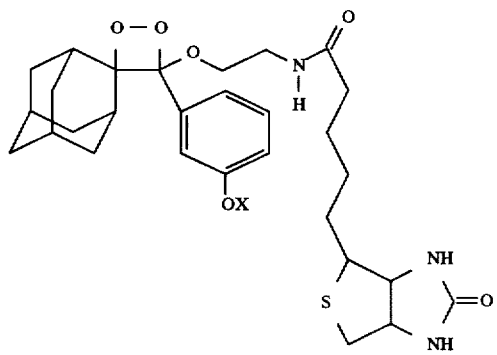

5

X = H

15

-continued

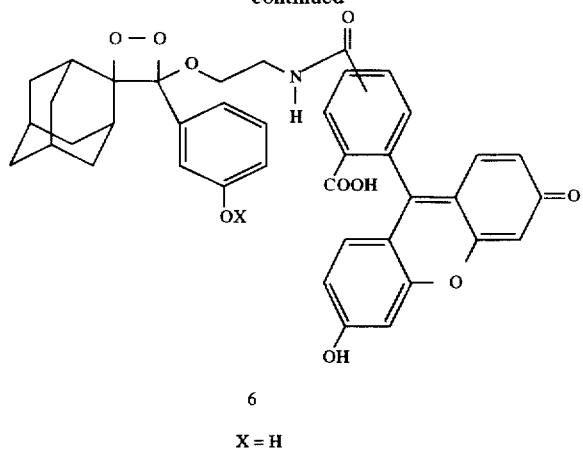

6

X = H

Instrumentation

Nuclear magnetic resonance (NMR) spectra were obtained on a General Electric QE300™ spectrometer as solutions in CDCl₃ with tetramethylsilane as internal standard unless noted otherwise. Mass spectra were obtained on either a Kratos MS-80™ or an AEI MS-90™ spectrometer. Weights were obtained on a Mettler AE 163™ analytical balance. Chemiluminescence measurements were performed using either a Turner or a device built in this laboratory which are interfaced to an Apple Macintosh™ computer.

Materials

Solvents and reagents obtained from various commercial sources were the best available grade and were used without further purification unless noted otherwise. Solvents were dried by distillation from sodium or calcium hydride.

Synthesis of Alkenes 2-Chloroethyl 3-hydroxybenzoate

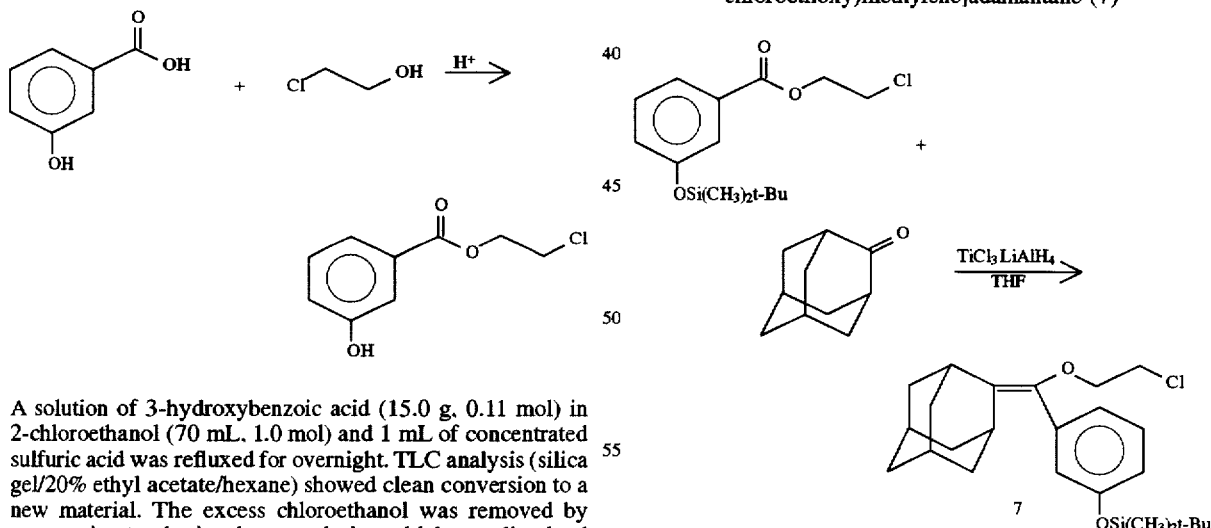

A solution of 3-hydroxybenzoic acid (15.0 g, 0.11 mol) in 2-chloroethanol (70 mL, 1.0 mol) and 1 mL of concentrated sulfuric acid was refluxed for overnight. TLC analysis (silica gel/20% ethyl acetate/hexane) showed clean conversion to a new material. The excess chloroethanol was removed by evaporation to obtain a brown solution which was dissolved in ethyl acetate and washed with water. The organic layer was dried with MgSO₄ and concentrated to obtain 21.0 g of the product as a white solid: mp 50° C.; ¹H NMR (CDCl₃) δ3.81 (t, 2H, J=5.9 Hz), 4.57 (t, 2H, J=5.9 Hz), 4.77 (s, 1H), 7.06–7.66 (m, 4H), ¹³C NMR (CDCl₃) δ41.52, 64.75, 116.43, 120.77, 121.98, 129.80, 130.71, 156.04, 166.57; MS m/e (rel. intensity) 200 (26), 138 (59), 121 (100), 93 (31), 65 (21), 39 (12); MS exact mass; calcd. 200.0240, found 200.0242.

16

2-Chloroethyl 3-(tert-butyldimethylsilyloxy)benzoate

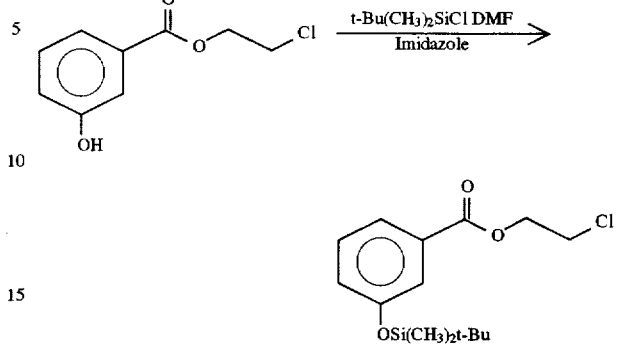

To a solution of 2-chloroethyl 3-hydroxybenzoate (4.0 g, 0.02 mol) and tert-butyldimthylsilyl chloride (4.5 g, 0.029 mol) in 5 mL of dry DMF imidazole (92.7 g, 0.04 mol) was gradually added. The solution was then stirred overnight. TLC analysis (silica gel, 20% ethyl acetate/hexane) showed clean conversion to a new material. The solution was poured into a 25 mL of water and extracted with ether (3×25 mL). The combined ether solutions were dried over anhydrous MgSO₄. Evaporation of the solvent gave an oil which was chromatographed on silica using (ethyl acetate/hexane, 10:90) to give the product quantitatively as a colorless liquid: ¹H NMR (CDCl₃) δ0.218 (s, 6H), 0.994 (s, 9H), 3.81 (t, 2H, J=5.7 Hz), 4.56 (t, 2H, J=5.7 Hz), 7.05–7.65 (m, 4H); ¹³C NMR (CDCl₃) δ–4.97, 17.66, 25.12, 41.06, 63.91, 120.61, 122.19, 124.60, 128.95, 130.53, 155.31, 165.35; MS m/e (rel. intensity) 314 (14), 257 (9), 235 (9), 213 (100), 185 (6), 149 (7), 135 (10), 120 (6), 93 (13), 83 (6), 69 (9), 55 (9); MS exact mass; calcd. 314.1104, found 314.1110.

[(3-tert-Butyldimethylsilyloxyphenyl)(2-chloroethoxy)methylene]adamantane (7)

A 100 mL three-necked flask fitted with a reflux condenser, was dried by means of a hot air gun and nitrogen purging. This was charged with dry THF 200 mL and cooled in an ice-bath. Titanium trichloride (24.5 g, 0.16 mol) followed by lithium aluminum hydride (3.0 g, 0.08 mol) was added in small portions with vigorous stirring. The cooling bath was removed and the black mixture was allowed to warm to room temperature. Triethylamine (15 mL) was added dropwise and the reaction mixture was refluxed for 1 hour. A solution of 2-chloroethyl 3-(tert-butyldimethylsilyloxy) benzoate (5.0 g, 0.015 mol) and adamantanone (7.1 g, 0.05 mol) was added dropwise to the refluxing mixture over a 1 hour period. TLC analysis (ethyl acetate/hexane, 10:90) after 1 hour of refluxing showed conversion to a new material. The reaction mixture was cooled, extracted with hexane. After the evaporation of solvent, the crude material was chromatographed using (ethyl acetate/hexane, 3:97) to give 5.0 g (74%) of alkene 7 as a white oil: $^1$H NMR (CDCl$_3$) δ0.194 (s, 6H), 0.982 (s, 9H), 1.78–1.98 (m, 12H), 2.65 (bs, 1H), 3.34 (bs, 1H), 3.55 (t, 2H, J=5.7 Hz), 3.66 (t, 2H, J=5.7 Hz), 6.85–7.29 (m, 4H); $^{13}$C NMR (CDCl$_3$) δ–4.46, 18.21, 25.66, 28.28, 30.20, 32.39, 38.94, 39.20, 42.61, 68.95, 119.62, 121.04, 122.50, 129.09, 132.78, 136.40, 141.11, 155.49; MS m/e (rel. intensity) 432 (100) 331 (22), 235 (13), 199 (10), 151 (19), 105 (17), 73 (44), 57 (14); MS exact mass: calcd. 432.2251, found 432.2247.

[(2-Chloroethoxy)(3-hydroxyphenyl)methylene] adamantane (8)

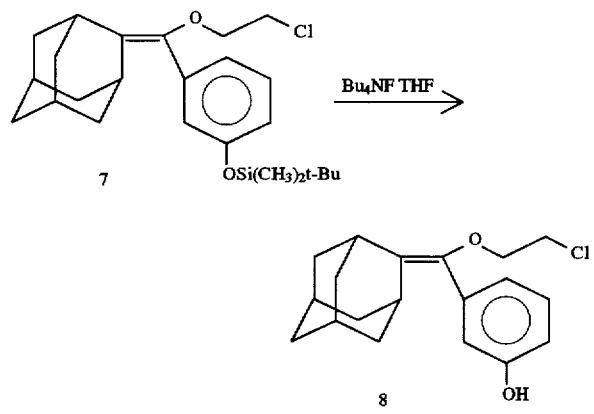

To a stirred solution of the tert-butyldimethylsilyl protected-alkene 7 shown above (2.0 g, 0.004 mol) in 5 mL of THF was added tetrabutylammonium fluoride trihydrate (TBAF, 1.4 g, 0.004 mol). The resulting solution was stirred for 10 minutes. TLC analysis (ethyl acetate/hexane, 20:80) indicated conversion to a new material. After evaporation of solvent, the crude product was washed with water and taken up in ether. The organic layer was dried over MgSO$_4$ and evaporated to dryness. The oily material was chromatographed on silica gel using (ethyl acetate/hexane, 20:80) to give 1.3 g (100%) of alkene 8: $^1$H NMR (CDCl$_3$) δ1.81–1.96 (m, 12H), 2.67 (bs, 1H), 3.34 (bs, 1H), 3.55 (t, 2H, J=5.6 Hz), 3.69 (t, 2H, J=5.6 Hz), 6.77–7.19 (m, 4H); $^{13}$C NMR (CDCl$_3$) δ28.21, 30.24, 32.35, 37.08, 38.92, 39.19, 42.55, 69.05, 114.76, 116.05, 121.92, 129.31, 133.41, 136.62, 140.77, 155.64; MS m/e (rel intensity) 318 (100), 227 (19), 213 (24), 121 (92), 107 (29), 93 (37), 69 (21), 55 (36), 41 (40); MS exact mass: calcd. 318.1386, found 318.1383.

[(3-Hydroxyphenyl)(2-iodoethoxy)methylene] adamantane (9)

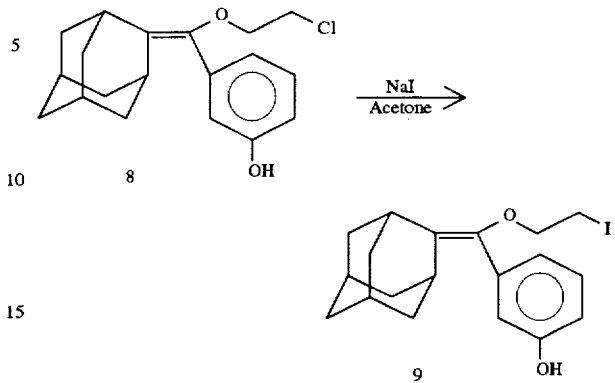

Sodium iodide (14.0 g, 0.09 mol) and [(2-chloroethoxy) (3-hydroxyphenyl) methylene] adamantane 8 (3.0 g, 0.009 mol) were dissolved in dry acetone and refluxed for 6 days. The reaction was followed by TLC analysis (ethyl acetate/ hexane, 10:90) and after the completion of reaction, solvent was evaporated to obtain a white solid. This solid was washed with methylene chloride several times and the combined organic layers were again washed with water. The organic layer was dried over MgSO$_4$ and concentrated to give 3.8 g (100%) of alkene 9 as an oily material: $^1$H NMR (CDCl$_3$) δ1.78–1.97 (m, 12H), 2.64 (bs, 1H), 3.19 (t, 2H, J=7.1 Hz), 3.35 (bs, 1H), 3.69 (t, 2H, J=7.1 Hz), 6.75–7.21 (m, 4H); $^{13}$C NMR (CDCl$_3$) δ2.40, 28.13, 30.41, 32.33, 36.99, 38.86, 39.09, 69.74, 114.86, 116.00, 121.79, 129.28, 133.37, 136.42, 140.51, 155.66; MS m/e (rel intensity) 410 (42), 256 (19), 227 (75), 155 (18), 121 (100), 107 (32), 93 (28), 79 (14), 65 (16); MS exact mass: calcd. 410.0744, found 410.0744.

[(2-Aminoethoxy)(3-hydroxyphenyl)methylene] adamantane (10)

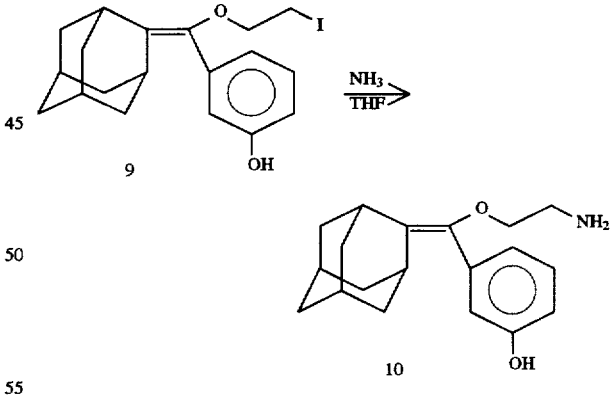

A solution of alkene 9 (3.0 g, 0.01 mol) in a minimum amount of THF was added into 10 mL of liquid ammonia in a sealed tube which was kept in dry ice. After sealing the tube this was heated at 40° C. in an oil bath for 17 hours. The reaction mixture was cooled down and solvent evaporated to obtain a white solid. This material was extracted with methylene chloride. The combined organic layers were washed with water, dried over MgSO$_4$, and concentrated to give 2.0 g (90%) of alkene 10 as a white solid: mp 55° C., $^1$H NMR (CDCl$_3$) δ1.77–1.96 (m, 12H), 2.68 (bs, 1H), 2.85 (t, 2H, J=4.8 Hz), 3.23 (bs, 1H), 3.48 (t, 2H, J=4.8 Hz), 4.46 (bs, 2H), 6.70–7.17 (m, 4H); $^{13}$C NMR (CDCl$_3$) δ28.16, 30.28, 32.19, 36.99, 38.88, 39.04, 41.33, 70.45, 114.97, 116.17, 120.63, 129.02, 131.89, 136.69, 141.79, 156.86; MS m/e (rel intensity) 299 (10), 256 (100), 239 (5), 199 (6), 135 (12), 121 (27), 93 (12), 77 (5); MS exact mass: calcd. 299.1885, found 299.1891.

3-Chloropropyl 3-hydroxybenzoate

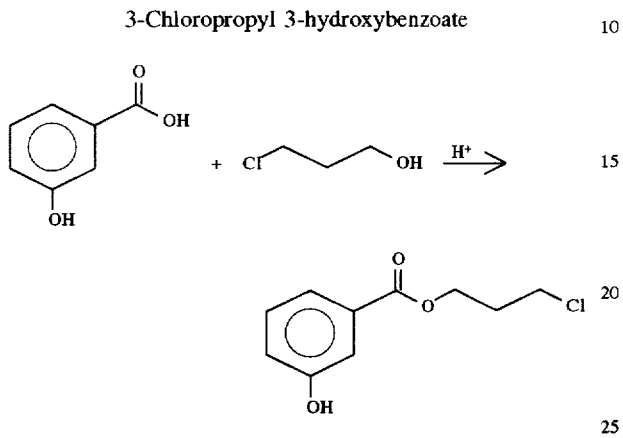

A solution of 3-hydroxybenzoic acid (16.0 g, 0.115 mol) in 3-chloropropanol (76 g, 0.81 mol) and 0.5 mL of concentrated sulfuric acid was refluxed overnight. The excess alcohol was removed by vacuum distillation. The brown viscous residue was dissolved in ethyl acetate (60 mL) and washed with water (2×15 mL). The organic layer was dried over anhydrous sodium sulfate, filtered and concentrated under reduced pressure. The brown viscous residue was purified by column chromatography (ethyl acetate/hexane, 30:70) to give the product as a white solid (23.3 g, 0.108 mol, 93.7%): $^1$H NMR (CDCl$_3$) δ2.19–2.28 (m, 2H), 3.69 (t, 2H, J=6.3 Hz), 4.48 (t, 2H, J=6Hz), 5.92 (s, 1H), 7.05–7.64 (m, 4H); MS exact mass: calcd. 214.0396, found 214.0400.

3-Chloropropyl 3-(tert-butyldimethylsilyloxy)benzoate

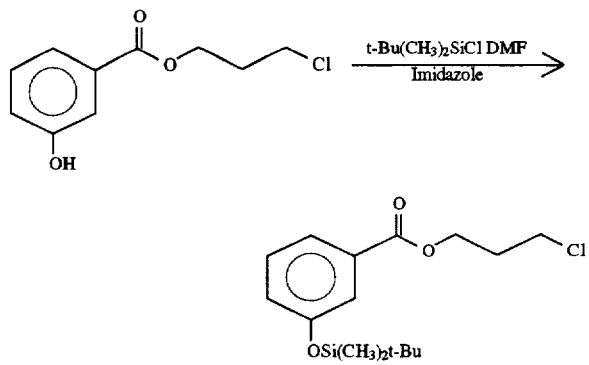

To a solution of 3-chloropropyl 3-hydroxybenzoate (12.0 g, 0.055 mol) and tert-butyldimethylsilyl chloride (TBDMS-Cl, 10.00 g, 0.067 mol) in anhydrous DMF (10 mL) was added imidazole (7.61 g, 0.11 mol). The reaction mixture was stirred for 1 hour after which it was diluted with water (50 mL) and extracted with hexane (4×20 mL). The hexane layer was washed with water (2×10 mL) and dried over anhydrous sodium sulfate, filtered and concentrated under reduced pressure to give the desired compound (16.64 g, 0.0506 mol, 90%): $^1$H NMR (CDCl$_3$) δ0.216 (s, 6H), 0.994 (s, 9H), 2.19–2.27 (m, 2H), 3.69 (t, 2H, J=6.3 Hz), 4.46 (t, 2H, J=6.3 Hz), 7.01–7.64 (m, 4H); MS exact mass: calcd. 328.1264, found 328.1257.

[3-tert-Butyldimethylsilyloxyphenyl)(3-chloropropoxy)methylene]adamantane (11)

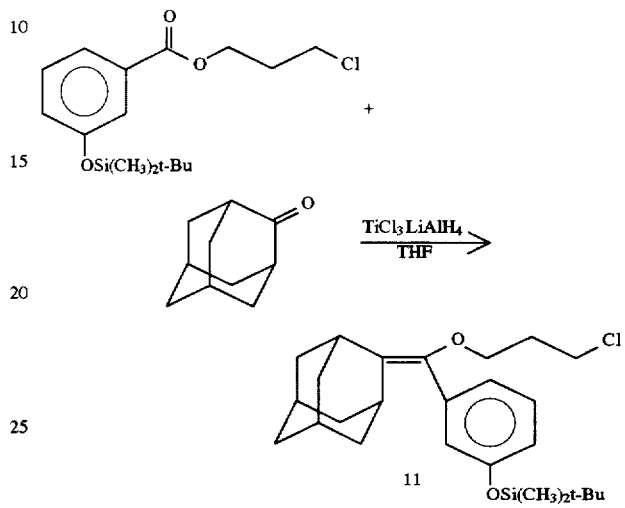

A 1 liter three-necked flask equipped with a reflux condenser was dried by means of a hot air gun and purged with argon. Anhydrous THF (200 mL) was added and cooled in an ice-bath. Titanium trichloride (33.32 g, 0.216 mol) was added with stirring. Lithium aluminum hydride (4.1 g, 0.108 mol) was added in small portions with vigorous stirring. The cooling bath was removed and the reaction mixture was allowed to warm to room temperature. Triethylamine (20 mL) was added dropwise and the reaction mixture was refluxed for 1 hour. A solution of 3-chloropropyl 3-tert-butyldimethylsiloxybenzoate (6.0 g, 0.018 mol) and adamantanone (8.22 g, 0.054 mol) in anhydrous THF was added dropwise to the refluxing mixture over a 1 hour period. The reaction mixture was refluxed for 1 hour and cooled to room temperature. Hexane (500 mL) was added and after stirring for 0.5 hour, the solution was filtered and concentrated under reduced pressure. The pale yellow residue was chromatographed (ethyl acetate/hexane, 3:97) to give alkene 11 as a viscous oil (4.7 g, 0.010 mol, 58.45%): $^1$H NMR (CDCl$_3$) δ0.19 (s, 6H), 0.98 (s, 9H), 1.76–2.01 (m, 14H), 2.62 (bs, 1H), 3.22 (bs, 1H), 3.52 (t, 2H, J=5.7 Hz), 3.63 (t, 2H, J=6.6 Hz}, 6.74–7.20 (m, 4H); MS exact mass: calcd. 446.2407, found 446.2414.

[(3-Chloropropoxy)(3-hydroxyphenyl)methylene]adamantane (12

21

-continued

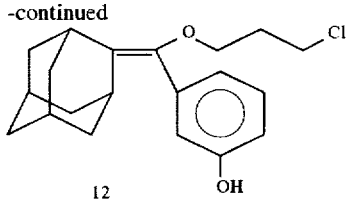

12

To a stirred solution of alkene 11 (0.5 g, 1 mmol) in anhydrous THF (15 mL), TBAF (0.32 g, 1.2 mmol, 1.22 mL of 1M solution) was added and the reaction mixture stirred for 0.5 hour at room temperature. The solvent was removed under reduced pressure and the residue was dissolved in hexane (20 mL). The solution was washed with water (10 mL) and the organic layer was dried over anhydrous sodium sulfate, filtered and concentrated under reduced pressure. The pale yellow oil was purified by preparative TLC (ethyl acetate/hexane, 20:80) to afford the pure compound 12 (0.34 g, 1 mmol, 92%): $^1$H NMR (CDCl$_3$) δ1.5–2.03 (m, 14H), 2.65 (bs, 1H), 3.22 (bs, 1H), 3.54 (t, 2H, J=6 Hz), 3.63 (t, 2H, J=6.6 Hz), 5.45 (s, 1H), 6.78–7.26 (m, 4H); MS exact mass: calcd. 332.1542, found 332.1540.

[(3-Cyanopropoxy)(3-hydroxyphenyl)methylene] adamantane (13

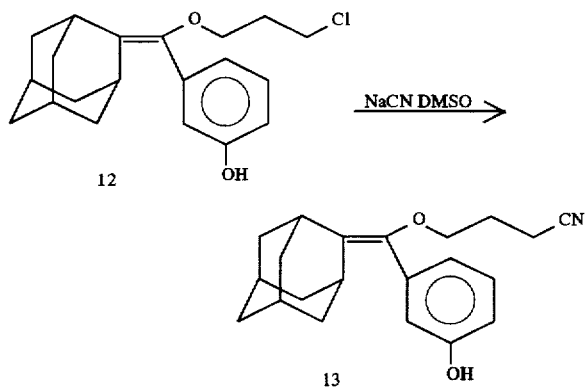

Sodium cyanide (9 mg, 0.19 mmol) was dissolved in anhydrous DMSO (2 mL) and the solution heated to 90° C. Alkene 12 (0.026 g, 0.078 mmol) was added to the above solution and the reaction mixture stirred at 90° C. for 0.75 hour. Water (15 mL) was added and extracted with ether (3×10 mL). The ether layer was washed with water (10 mL) and dried over anhydrous sodium sulfate, filtered and concentrated under reduced pressure. Purification by preparative TLC (ethyl acetate/hexane, 20:80) gave pure nitrile 13 (0.021 g, 0.065 mmol, 84%): $^1$H NMR (CDCl$_3$) δ1.6–2.03 (m, 14H), 2.48 (t, 2H, J=7.2 Hz), 2.64 (bs, 1H), 3.18 (bs, 1H), 3.49 (t, 2H, J=6 Hz), 4.99 (s, 1H), 6.78–7.26 (m, 4H); IR (CHCl$_3$) cm$^{-1}$3660-3600, 3000, 2910, 2840, 2290, 1420, 1200, 1100; MS exact mass: calcd. 323.18852, found 323.1882.

22

[(3-Carboxypropoxy)(3-hydroxyphenyl)methylene] adamantane (14)

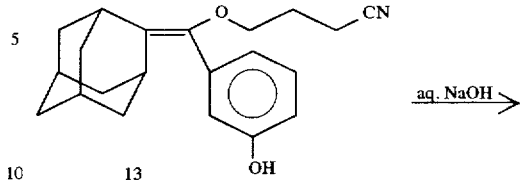

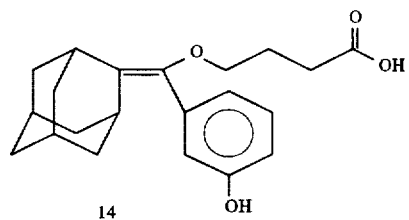

Sodium hydroxide (2 mL of a 2 N solution) was added to the nitrile 13 (0.018 g, 0.055 mmol) and the reaction mixture was refluxed for 1 hour. The solution was cooled to room temperature and diluted with water (5 mL). The aqueous solution was washed with dilute acid (10 mL) and the white turbid solution immediately extracted with ethyl acetate (2–15 mL). The organic layer was dried over anhydrous sodium sulfate, filtered and concentrated under reduced pressure. The crude residue was purified by preparative TLC (ethyl acetate/hexane, 30:70) to afford pure acid 14 (0.012 g, 0.035 mmol, 63%): $^1$H NMR (CDCl$_3$) δ1.6–2.03 (m, 16H), 2.44 (t, 2H, J=7.2 Hz), 2.65 (bs, 1H), 3.21 (bs, 1H), 3.45 (t, 2H, J=6 Hz), 6.1–7.41 (m, 5H); MS exact mass: calcd. 342.1831, found 342.1836.

[(3-Carboxypropoxy)(3-hydroxyphenyl)methylene] adamantane N-hydroxysuccinimide Ester 15

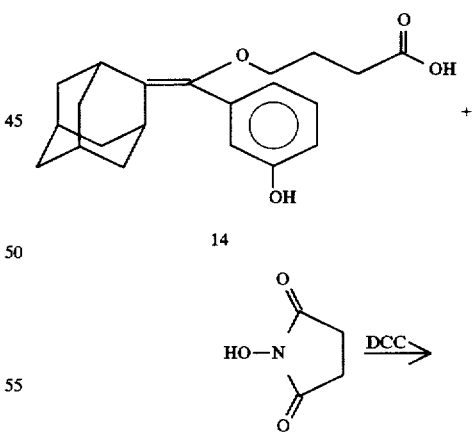

23

-continued

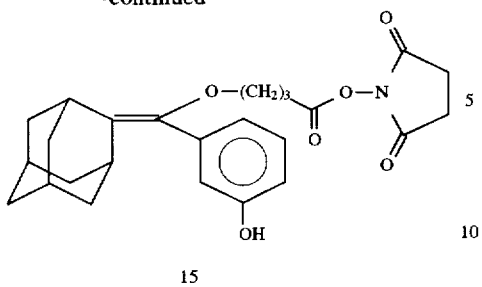

15

24

[(3-tert-Butyldimethylsilyloxyphenyl)(3-carboxypropoxy)methylene]adamantane (17)

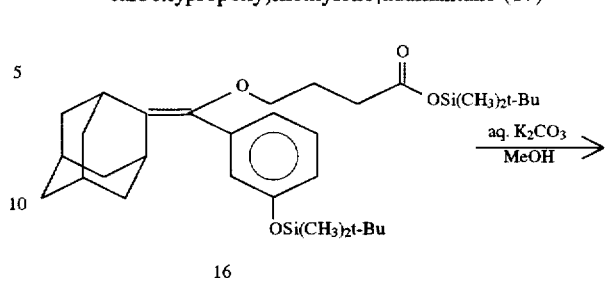

16

Carboxylic acid 14 (0.008 g, 0.02 mmol) was dissolved in anhydrous dioxane (1 mL). Dicyclohexylcarbodiimide (DCC, 0.0072 g, 0.035 mmol) and N-hydroxysuccinimide (0.004 g, 0.035 mmol) were added to the above solution and stirred at room temperature for 12 hours under argon. The white precipitates were filtered and the solution was concentrated under reduced pressure. The residue was purified by preparative TLC (methanol/dichloromethane, 2:98) to afford pure product 15 (0.009 g, 0.02 mmol, 88%): $^1$H NMR (CDCl$_3$) δ1.71–2.05 (m, 14H), 2.68 (bs, 1H), 2.78 (t, 2H, J=7.2 Hz), 2.86 (bs, 4H), 3.21 (bs, 1H), 3.47 (t, 2H, J=6 Hz), 5.90 (bs, 1H), 6.78–7.26 (m, 4H); $^{13}$C NMR (CDCl$_3$) δ24.56, 25.47, 27.44, 28.14, 30.23, 32.15, 37.00, 38.83, 39.04, 66.90, 67.23, 90.64, 114.52, 115.72, 121.34, 128.97, 132.07, 136.75, 141.54, 155.98, 168.41, 169.54; MS exact mass: calcd. 439.1994, found 439.1988.

Alkene 16.

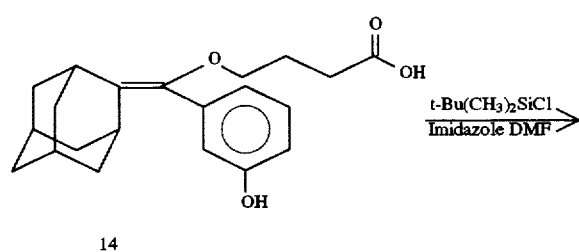

14

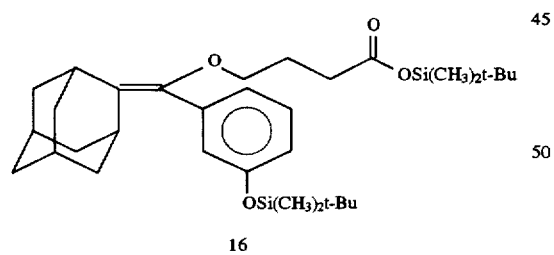

16

Imidazole (0.015 g, 0.22 mmol) and TBDMS chloride (0.033 g, 0.22 mmol) were added to a solution of alkene 14 (0.025 g, 0.07 mmol) dissolved in anhydrous DMF (2 mL) and stirred at room temperature for 2 hours. The reaction mixture was diluted with water (10 mL) and extracted with ethyl acetate (2×12 mL). The organic layer was washed with water (7 mL) and dried over anhydrous sodium sulfate, filtered and concentrated under reduced pressure. Attempts to purify the residue by preparative TLC resulted in decomposition. Therefore, crude product 16 was used directly for the next step.

Bis-silyloxy alkene 16 (0.039 g, 0.068 mmol) was dissolved in methanol (5 mL) and K$_2$CO$_3$ (2 eq) dissolved in H$_2$O (2 mL) was added. The reaction mixture was stirred at room temperature for 10 minutes. (TLC showed no trace of starting material). The solution was quenched with dilute acid (7 mL) and extracted with ethyl acetate (2×10 mL). The organic layer was washed with H$_2$O (5 mL), dried over anhydrous sodium sulfate, filtered and concentrated under reduced pressure to afford 17 (0.025 g, 0.043 mmol, 83%): $^1$H NMR (CDCl$_3$) δ0.19 (S, 6H), 0.98 (S, 9H), 1.77–1.97 (m, 14H), 2.45 (t, 2H, J=7.5 Hz), 2.62 (bs, 1H), 3.22 (bs, 1H), 3.42 (t, 2H, J=6.0 Hz), 6.74–7.21 (m, 4H); MS exact mass: calcd. 456.2695, found 456.2692.

[(3-t-Butyldimethylsilyloxyphenyl)(3-carboxypropoxy)methyleneadamantane N-hydroxysuccinimide Ester 18.

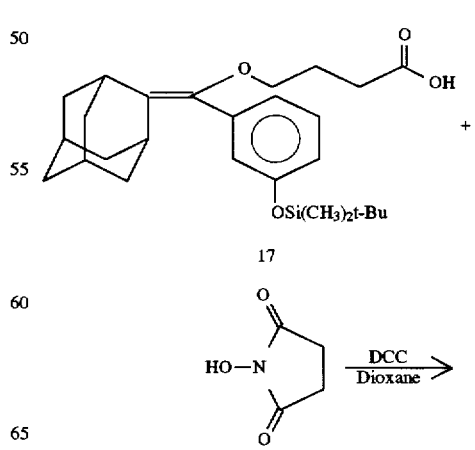

25

-continued

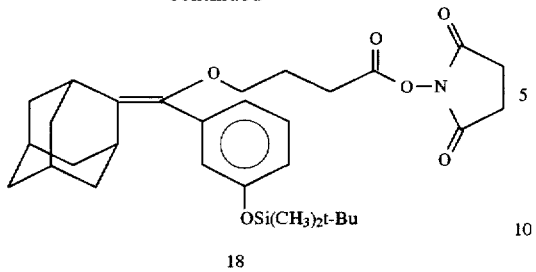

18

Carboxylic acid 17 (0.025 g, 0.056 mmol) was dissolved in anhydrous dioxane (1 mL). DCC (0.023 g, 0.11 mmol) and N-hydroxysuccinimide (0.013 g, 0.11 mmol) were added to the above solution and stirred at room temperature for 8 hours under argon. The white precipitate was filtered and the solution was concentrated under reduced pressure. The residue was purified by preparative TLC (ethyl acetate/hexane, 40:60) to afford alkene 18 (0.028 g, 0.050 mmol, 90%): $^1$H NMR (CDCl$_3$) δ0.18 (S, 6H), 0.97 (S, 9H), 1.76–1.95 (m, 14H), 2.61 (bs, 1H), 2.72 (t, 2H, J=7.8 Hz), 2.82 (bs, 4H), 3.21 (bs, 1H), 3.45 (t, 2H, J=5.7 Hz), 6.74–7.26 (m, 4H); $^{13}$C NMR (CDCl$_3$) δ24.89, 25.55, 25.65, 27.94, 28.28, 30.27, 32.30, 33.90, 37.14, 38.92, 39.16, 49.17, 67.42, 104.93, 119.41, 121.02, 122.43, 123.84, 129.03, 131.91, 136.83, 141.66, 155.35, 168.47, 169.04.

Alkene 19.

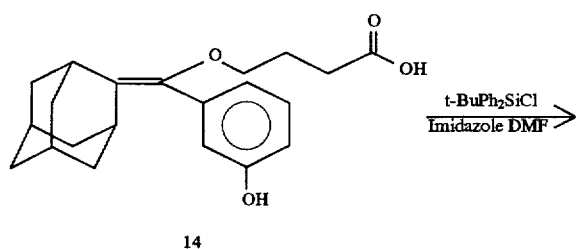

14

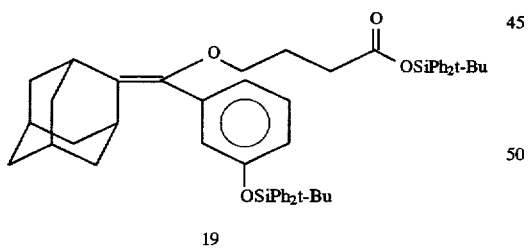

19

Imidazole (0.053 g, 0.00078 mol) and t-butyldiphenylsilyl chloride (0.216, g, 0.00078 mol) were added to a solution of acid 14 (0.090 g, 0.00026 mol) dissolved in anhydrous DMF (2 mL) and stirred at room temperature for 2 hours. The reaction mixture was diluted with water (6 mL) and extracted with ethyl acetate (3×10 mL). The organic layer was washed with water (7 mL) and dried over anhydrous sodium sulfate, filtered and concentrated under reduced pressure. Attempts to purify the residue by preparative TLC resulted in decomposition. Therefore, crude product 19 was used directly for the next step.

26

[(3-tert-Butyldiphenylsilyloxyphenyl)(3-carboxypropoxy)methylene]adamantane (20)

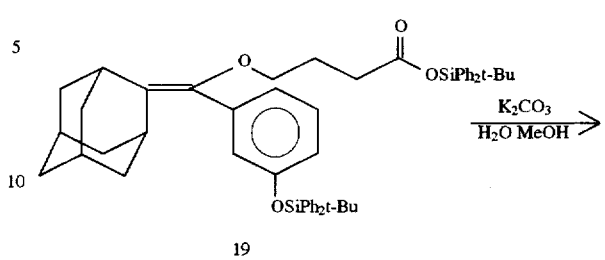

19

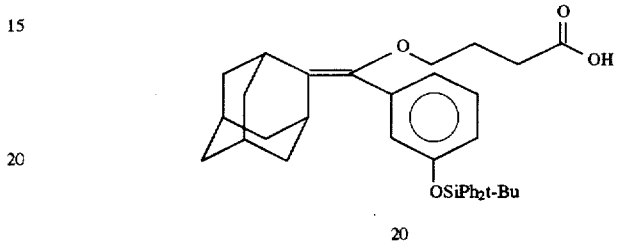

20

Bis-silyloxy alkane 19 (0.215 g, 0.00026 mol) was dissolved in methanol (5 mL) and K$_2$CO$_3$ (2 eq.) dissolved in H$_2$O (2 mL) was added. The reaction mixture was stirred at room temperature for 20 minutes (TLC showed no trace of starting material). The solution was quenched with dilute acid (7 mL) and extracted with ethyl acetate (2×20 mL) The organic layer was washed with H$_2$O (7 mL), dried over anhydrous sodium sulfate, filtered and concentrated under reduced pressure to afford 20 (0.12 g, 0.0002 mol, 80%): $^1$H NMR (CDCl$_3$) δ1.10 (s, 9H), 1.49–1.88 (m, 14H), 2.31 (bs, 1H), 2.34 (d, 2H), 3.10 (bs, 1H), 3.18 (t, 2H, J=6Hz), 6.60–7.71 (m, 14H), 10.5 (bs, 1H); MS exact mass: calcd. 580.3008, found 580.3012.

[(3-tert-Butyldiphenylsilyloxyphenyl)(3-carboxypropoxy)methylene]adamantane N-hydroxysuccinimide Ester (21)

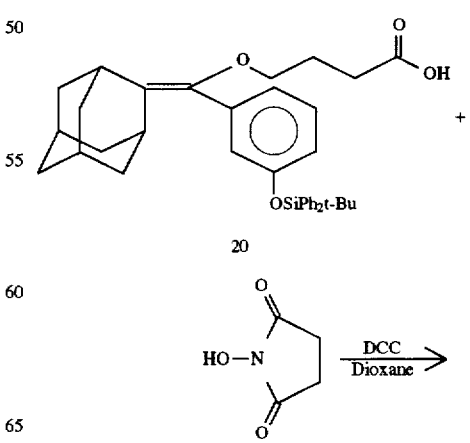

27
-continued

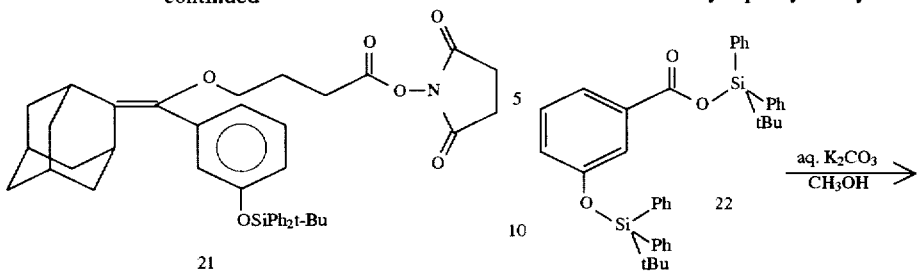

Carboxylic acid 20 (0.070 g, 0.00012 mol) was dissolved in anhydrous dioxane (4 mL). DCC (0.075 g, 0.00036 mol) and N-hydroxysuccinimide (0.041 g, 0.00036 mol) were added to the above solution and stirred at room temperature for 12 hours under argon. The white precipitate was filtered and the solution was concentrated under reduced pressure. The residue was purified by preparative TLC (methanol/dichloromethane, 3:97) to afford 21 (0.071 g, 0.00010 mol, 88%): $^1$H NMR (CDCl$_3$) δ1.10 (s, 9H), 1.50–1.95 (m, 14H), 2.36 (bs, 1H), 2.58 (t, 2H, J=7.2 Hz), 2.82 (bs, 4H), 3.09 (bs, 1H), 3.19 (t, 2H, J=6 Hz), 6.58–7.71 (m, 14H); $^{13}$C NMR (CDCl$_3$) δ19.36, 24.69, 24.90, 25.53, 26.43, 27.83, 28.16, 30.10, 32.07, 33.91, 37.07, 38.79, 38.93, 67.15, 119.02, 120.85, 122.13, 127.69, 128.90, 129.84, 131.63, 132.77, 135.52, 136.39, 141.37, 155.24, 168.45, 169.03; MS exact mass: calcd. 677.8339, found M-239.

tert-butyldiphenylsiloxy 3-(tert-butyldiphenyl-siloxy)benzoate (22)

Imidazole (1.23 g, 0.018 mol) and DPTBS chloride (4.97 g, 0.018 mol) were added to a solution of m-hydroxy benzoic acid (1.0 g, 0.0072 mol) dissolved in anhydrous DMF (10 mL) and stirred at room temperature for 4 hours. The reaction mixture was diluted with water (10 mL) and extracted with ethyl acetate (2×15 mL). The organic layer was washed with water (10 ML) and dried over anhydrous sodium sulfate, filtered and concentrated under reduced pressure. Purification by chromatography (ethyl acetate/hexane, 10:90) gave 22 (4.38 g, 0.0071 mol, 98%). $^1$H NMR (CDCl$_3$) δ1.10 (s, 9H), 1.18 (s, 9H), 7.01–7.79 (m, 24H). M.S. Exact mass: calculated 614., found M-57,557.

28
3-tert butyldiphenylsiloxybenzoic acid (23)

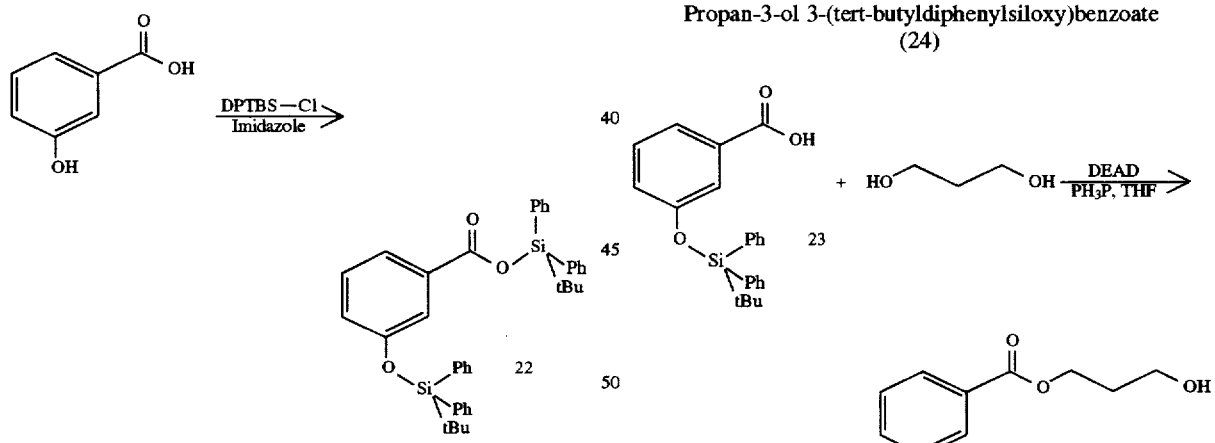

The bis-siloxy compound 22 (4.0 g, 0.0065 mol) was dissolved in methanol (25 mL) and K$_2$CO$_3$ (2 eq) dissolved in H$_2$O (10 mL) was added. The reaction mixture was stirred at room temperature for 20 minutes. (TLC showed no trace of starting material.) The solution was quenched with dilute acid (20 mL) and extracted with ethyl acetate (3×20 mL). The organic layer was washed with H$_2$O (15 mL), dried over anhydrous sodium sulfate, filtered and concentrated under reduced pressure to afford 23 (2.43 g, 0.0064 mol, 99%). $^1$H NMR (CDCl$_3$) δ1.13 (s, 9H), 6.88–7.74 (m, 14H), 9.7 (bs, 1H). M.S. Exact mass: calculated 376.1495, found 376.1500.

Propan-3-ol 3-(tert-butyldiphenylsiloxy)benzoate (24)

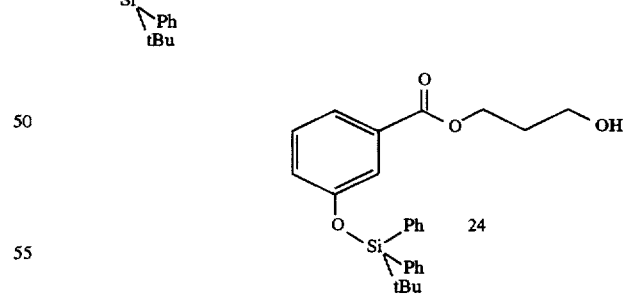

DEAD (0.14 g, 0.00079 mol) was added to a solution of acid 23 (0.3 g, 0.00079 mol) dissolved in anhydrous THF (10 mL). A mixture of triphenylphosphine (0.21 g, 0.0008 mol) and 1,3-propanediol (0.091 g, 0.0011 mol) in THF (3 mL) was injected slowly to the above solution and reaction mixture stirred at room temperature for 24 hours. The solution was quenched with H$_2$O (12 mL) and extracted with ethyl acetate (2×15 mL). The organic layer was dried over anhydrous Na$_2$SO$_4$ and concentrated under reduced pressure. Purification by preparative TLC (ethylacetate/hexane, 70:30) gave the pure ester (24) (0.25 g, 0.00058 mol, 73%). $^1$H NMR (CDCl$_3$) δ1.11 (s, 9H), 1.88–1.96 (m, 2H), 2.49 (bs, 1H), 3.67 (t, 2H, J=6 Hz), 4.38 (t, 2H, J=6Hz), 6.86–7.72 (m, 14H). M.S. Exact mass: calculated 434.4126, found M+l, 435.

|(3-Hydroxypropoxy)(3-tert-butyldiphenyl-siloxyphenyl)methylene|adamantane (25)

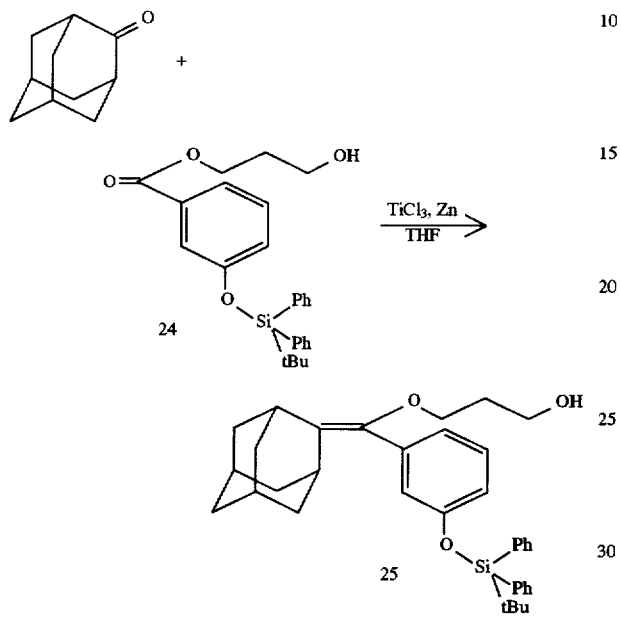

A 100 mL three-necked flask equipped with a reflux condensor was dried with a hot air gun and purged with argon. Titanium trichloride (1.10 g, 0.0068 mol) was added to anhydrous THF (15 mL) with stirring. In dust (0.70 g, 0.010 mol) was added and solution stirred in a warm water bath for 15 minutes. The solution was cooled (ice bath) and anhydrous triethylamine (1 mL) injected slowly. After stirring for 10 minutes at 0° C., the solution was allowed to warm to room temperature and refluxed under argon for 2 hours. A solution of the ester (24) (0.85 g, 0.0019 mol) and adamantanone (0.44 g, 0.0029 mol) dissolved in anhydrous THF (5 mL) was added dropwise and reaction mixture refluxed for 4 hours. The solution was cooled to room temperature and hexane (20 mL) was added. The black slurry was dissolved in H$_2$O (20 mL) and extracted with ether (3×10 mL). The organic layer was filtered and solution concentrated under reduced pressure. Purification by preparative TLC (ethyl acetate/hexane, 30:70) afforded 25 (0.14 g, 0.00025 mol, 12%). $^1$H NMR (CDCl$_3$)δ 1.12 (s, 9H), 1.50–2.1 (m, 15H), 2.37 (bs, 1H), 3.11 (bs, 1H), 3.32 (t, 2H, J=6 Hz), 3.64 (t, 2H, J=6 Hz), 6.64–7.73 (m, 14H). $^{13}$C (CDCl$_3$) δ 19.34, 26.43, 28.15, 30.13, 30.95, 32.05, 32.22, 36.45, 38.83, 38.91, 61.10, 67.50, 118.98, 120.92, 122.03, 127.64, 128.86, 129.78, 131.59, 132.81, 135.49, 136.58, 141.71, 155.22.

M.S. Exact mass: calculated 552.3059, found 552.3066.

Biotin amide alkene (26)

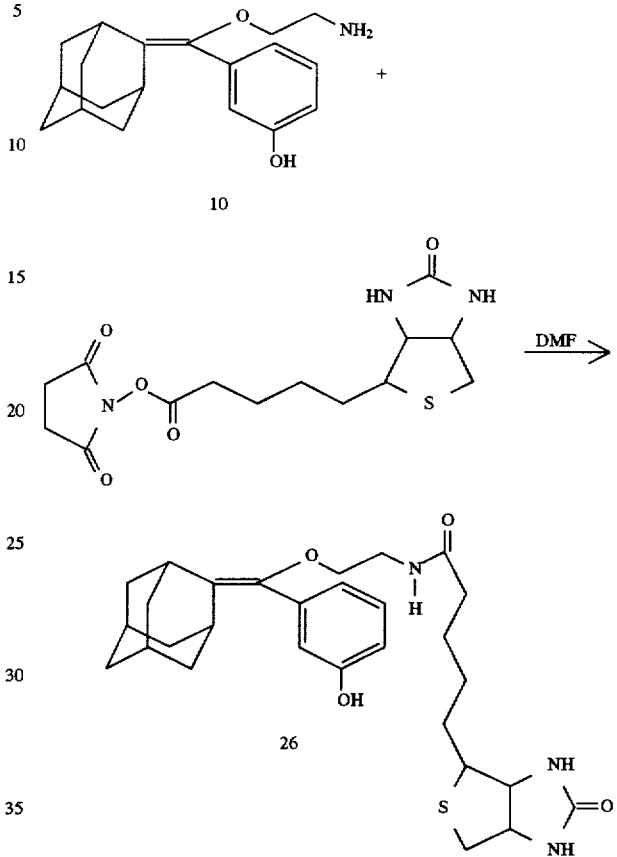

Biotin NHS ester (Cal Biochem) (0.025 g, 0.073 mmol) was added to a solution of the amino alkene 10 (0.012 g, 0.04 mmol) dissolved in anhydrous DMF (4 mL). The reaction mixture was stirred under argon for 48 hours. Water (5 mL) was added and extracted with dichloromethane (2×12 mL). The organic layer was dried over anhydrous Na$_2$SO$_4$ and concentrated under reduced pressure. The pale yellow residue was purified by preparative TLC (methanol/dichloromethane, 10:90) to afford 26 (0.019 g, 0.036 mmol, 73%) as a white solid. $^1$H NMR (CDCl$_3$) δ1.25–2.17 (m, 20H), 2.65–2.94 (m, 3H), 3.12–3.59 (m, 6H), 4.31–4.35 (m, 1H), 4.50–4.54 (m, 1H), 5.26 (bs, 1H), 6.17 (t, 1H, J=2.4 Hz), 6.40 (bs, 1H), 6.75–7.32 (m, 4H). $^{13}$C (CDCl$_3$) δ25.45, 27.91, 28.16, 30.43, 32.25, 35.84, 37.02, 39.11, 39.57, 40.50, 55.64, 60.31, 61.95, 68.73, 115.03, 115.79, 120.91, 129.09, 133.28, 136.90, 141.70, 156.90, 164.49, 173.86. M.S. Exact mass: calculated 525.7158, found FAB (M+23 [Na]) 548.6.

31

Fluorescein amide alkene (27)

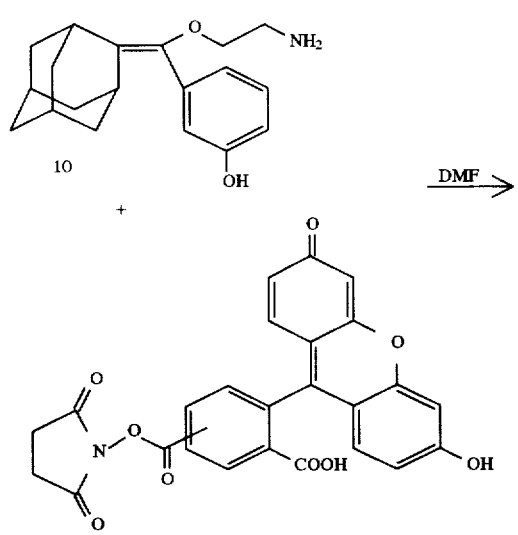

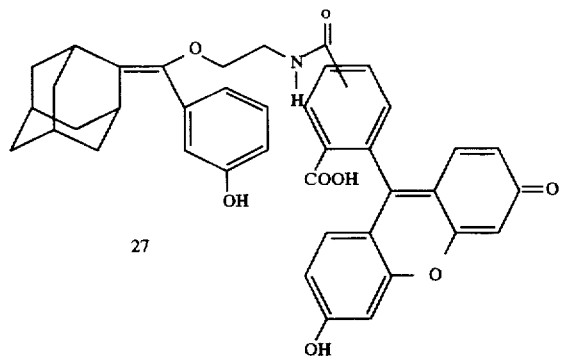

To a solution of the amino alkene 10 (0.012 g, 0.00004 mol) in anhydrous dichloromethane/DMF (3:1, 3 mL), 5 (and-6) carboxy-fluorescein succinimidyl ester (Molecular Probes) (0.030 g, 0.00006 mol) was added and the reaction mixture stirred under argon at room temperature for 24 hours. The solution was quenched with water (5 mL) and extracted with ethyl acetate (2×12 mL). The organic layer was dried over anhydrous sodium sulfate and concentrated under reduced pressure. Purification by preparative TLC (methanol/dichloromethane, 10:90), gave the alkene 27 (0.015 g, 0.000022 mol, 58%). $^1$H NMR (CD$_3$OD) δ1.27–1.96 (m, 12H), 2.60 (bs, 1H), 3.07 (bs, 1H), 3.56–3.62 (m, 4H), 6.51–8.46 (m, 13H). M.S. Exact mass: calculated 657.7268, found FAB (M+1) 658.

Preparation of 1,2-Dioxetanes

The dioxetanes are prepared by the photooxygenation procedures illustrated below. Each of the alkenes shown above can be converted to the corresponding dioxetane.

32

Dioxetane 1a

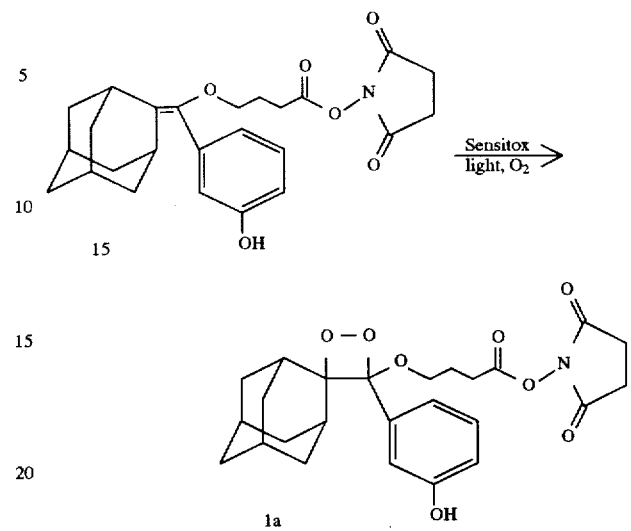

Alkene 15 (0.012 g, 0.027 mmol) dissolved in anhydrous dichloromethane (4 mL) was irradiated with a 1000 W sodium lamp at −78° C. in the presence of Sensitox with continuous bubbling of oxygen. After irradiation for 1 hour, the sensitizer was removed by filtration and the solvent evaporated to give dioxetane 1a (0.012 g, 0.027 mmol, 99%): $^1$H NMR (CDCl$_3$) δ1.05–2.12 (m, 14H), 2.18 (bs, 1H), 2.88 (bs, 4H), 3.03 (bs, 1H), 3.32–3.39 (m, 2H), 3.45–3.57 (m, 2H), 6.8–7.32 (m, 4H); $^{13}$C NMR (CDCl$_3$) δ25.59, 25.83, 25.97, 31.56, 31.81, 32.20, 32.91, 33.05, 34.68, 36.36, 38.92, 67.23, 95.60, 111.40, 116.81, 121.61, 129.61, 135.94, 156.12, 168.36.

Dioxetane 1b

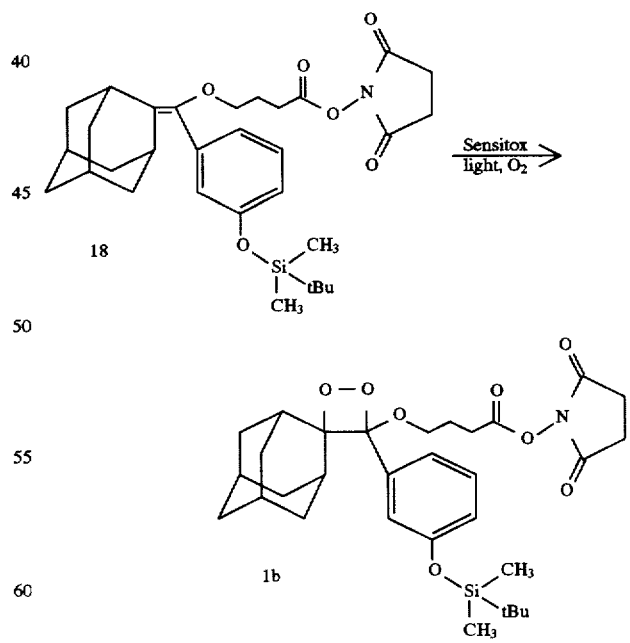

Alkene 18 (0.03 g, 0.054 mmol) dissolved in anhydrous dichloromethane (15 mL) was irradiated with a 1000 W sodium lamp at −78° C. in the prescence of Sensitox with continuous bubbling of oxygen. After irradiation for 2 hours, the sensitizer was removed by filtration and the solvent evaporated to give a quantitative yield of dioxetane 1b (0.028 g, 0.047 mmol, 88%): ¹H NMR (CDCl₃) δ0.18 (S, 6H), 0.97 (S, 9H), 1.70–2.1 (m, 14H), 2.28 (bs, 1H), 2.68–2.74 (m, 2H), 2.83 (bs, 4H), 3.01 (bs, 1H), 3.44–3.54 (m, 2H), 6.71–7.40 (m, 4H).

Dioxetane 1c

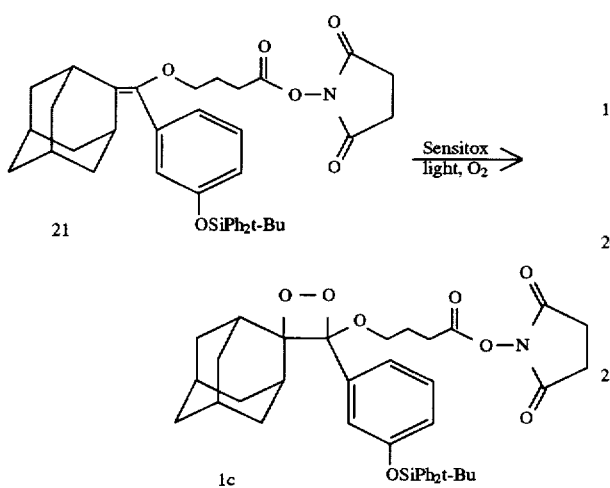

Alkene 21 (0.03 g, 0.044 mmol) dissolved in anhydrous dichloromethane (15 mL) was irradiated with a 1000 W sodium lamp at −78° C. in the presence of Sensitox with continuous bubbling of oxygen. After irradiation for 2 hours, the sensitizer was removed by filtration and the solvent evaporated to give quantitative yield of dioxetane 1c (0.031 g, 0.044 mmol, 99%): ¹H NMR (CD₂Cl₂) δ1.08 (s, 9H), 1.36–2.0 (m, 15H), 2.85 (m, 7H), 3.47 (m, 2H), 7.0–7.78 (m, 14H).

Dioxetane 2a

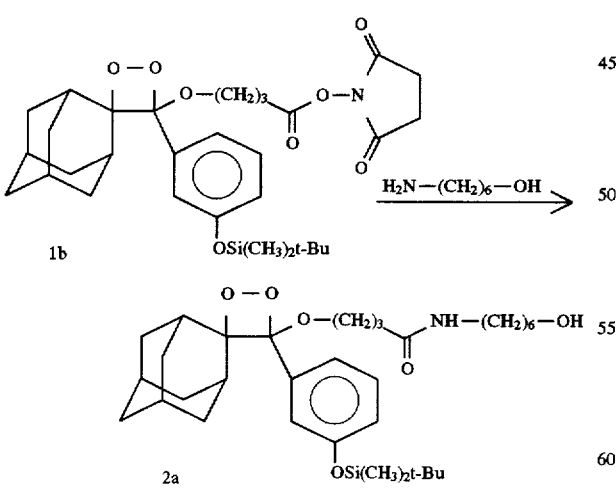

6-Aminohexanol (1.2 mg, 0.010 mmol) was added to a solution of the dioxetane 1b (0.004g, 0.0068 mmol) dissolved in anhydrous dichloromethane (2 mL) under argon. The reaction mixture was stirred at room temperature for 10 minutes. White precipitates were removed by filtration and the solution was concentrated under reduced pressure. Purification by preparative TLC (methanol/dichloromethane, 10:90) afforded 2a (0.004 g, 0.0068 mmol, 100%): ¹H NMR (CDCl₃) δ0.21 (S, 6H), 0.98 (S, 9H), 1.24–1.57 (m, 22H), 2.12 (t, 2H, J=6.6 Hz), 2.16 (bs, 1H), 2.30 (t, 2H, J=7.2 Hz), 3.26 (q, 2H, J=6.3 Hz), 3.60–3.66 (m, 3H), 4.35 (t, 2H, J=6.3 Hz), 5.5 (bs, 1H), 7.02–7.63 (m, 4H).

Dioxetane 2b

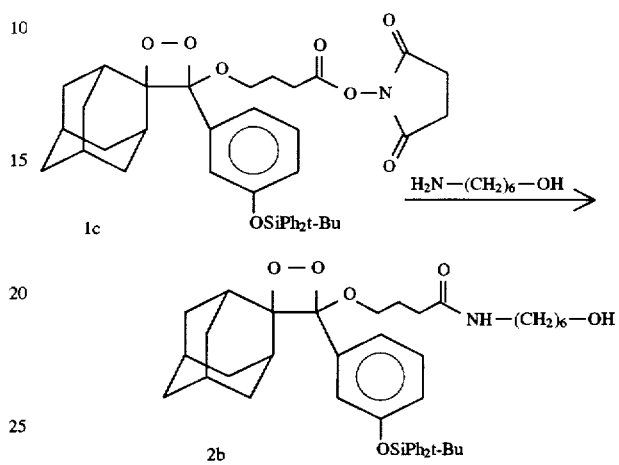

6-Aminohexanol (1 mg, 0.0084 mmol) was added to a solution of dioxetane 1c (2 mg, 0.0028 mmol) dissolved in anhydrous dichloromethane (2 mL) under argon. The reaction mixture was stirred at room temperature for 30 minutes. White precipitates were removed by filtration and the solution was concentrated under reduced pressure. Purification by preparative TLC (methanol/dichloromethane, 10:90) gave 2b (1.9 mg, 0.0026 mmol, 95%): ¹H NMR (CDCl₃) δ1.08 (s, 9H), 1.25–1.66 (m, 22H), 3.18–3.25 (m, 5H), 3.63 (t, 3H, J=6.0 Hz), 5.81 (t, 1H), 7.32–7.69 (m, 14H).

Dioxetanes 3a–c

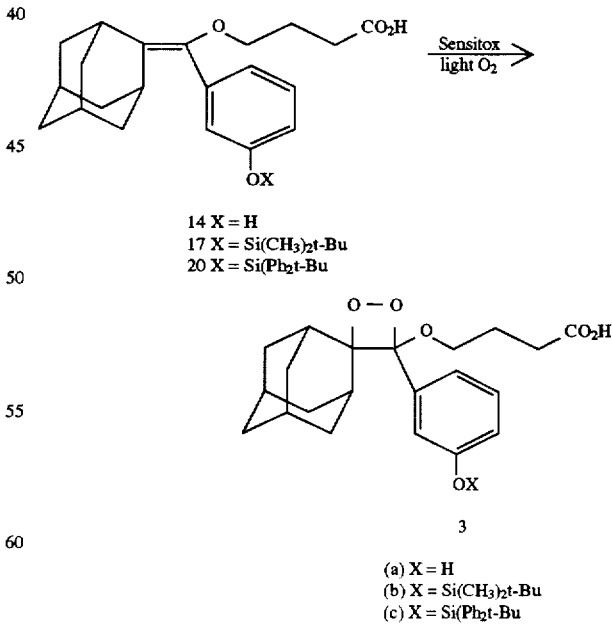

The dioxetanes 3a, 3b and 3c can be obtained from the alkenes 14, 17 and 20, respectively, by standard sensitized singlet oxygenation procedures.

Dioxetane 4

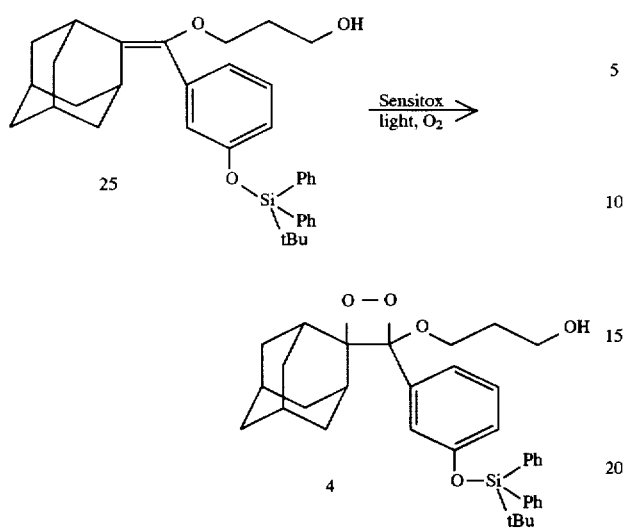

Alkene 25 (0.12 g, 0.0002 mol) dissolved in anhydrous dichloromethane (10 mL) was irradiated with a 1000 W sodium lamp at −78° C. in the presence of Sensitox with continuous bubbling of oxygen. After irradiation for 2.5 hours, the sensitizer was removed by filtration and the solution concentrated under reduced pressure. Purification by preparative TLC (ethyl acetate/hexane, 30:70) gave the dioxetane 4 (0.11 g, 0.00019 mol, 93%). $^1$H NMR (CDCl$_3$) δ1.09 (s, 9H), 1.36–2.09 (m, 16H), 2.81–3.86 (m, 5H), 7.31–7.74 (m, 14H). $^{13}$C NMR (CDCl$_3$) δ19.25, 25.68, 25.89, 26.32, 27.44, 30.94, 31.41, 31.60, 32.20, 32.67, 32.78, 34.40, 36.29, 36.44, 37.53, 59.97, 74.44, 77.20, 95.41, 111.56, 127.77, 129.92, 132.44, 135.34, 135.48, 135.99, 155.58.

Dioxetane 5

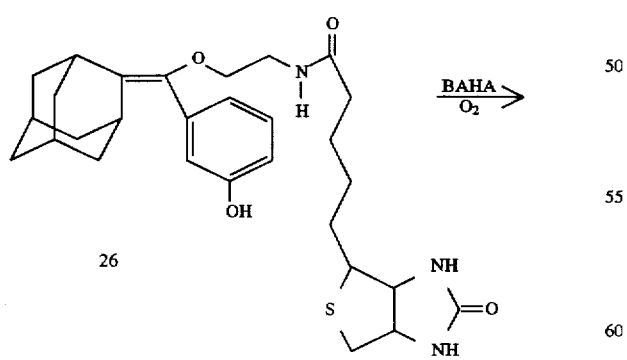

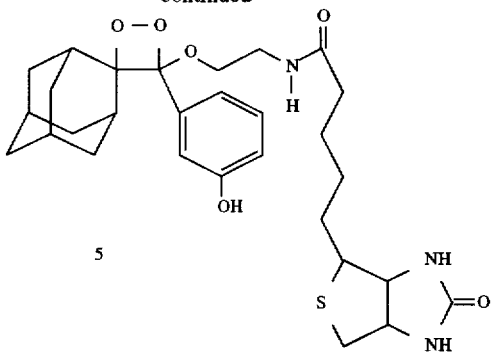

The biotinylated dioxetane 5 was obtained from the alkene 26. Anhydrous K$_2$CO$_3$ (0.15g) was added to the alkene 26 (0.012 g, 0.022 mmol) dissolved in anhydrous CH$_2$Cl$_2$ (10 mL) and oxygen bubbled for 2 minutes at 0° C. Tris(4-bromophenyl) ammonium hexachloroantimonate (BAHA) (0.004 g, 0.0048 mmol) was added to the above solution and O$_2$ bubbled into the reaction mixture for 30 minutes at 0° C. The solution was filtered and concentrated under reduced pressure. Purification by preparative TLC (methanol/CH$_2$Cl$_2$, 15:85) gave the dioxetane 5 (0.0091 g, 0.0163 mmol, 72%).

$^1$H NMR (CD$_3$OD/CDCl$_3$, 10:90) δ1.02–1.90 (m, 18H), 2.23–2.28 (m, 3H), 2.72 (d, 1H, J=12.9 Hz), 3.14–3.20 (m, 1H), 3.39–3.56 (m, 6H), 4.30–4.34 (m, 1H), 4.48–4.52 (m, 1H), 6.87–7.28 (m, 4H).

Dioxetane 6

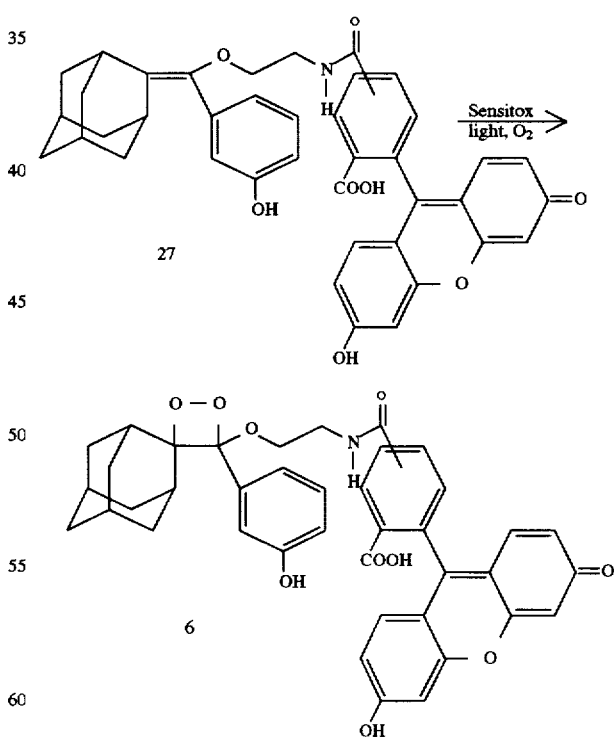

The alkene 27 (0.011 g, 0.0167 mmol) dissolved in a mixture of dichloromethane/methanol (9:1, 12mL) was irradiated with a 1000 W sodium lamp at -78° C. in the presence of Sensitox with continuous bubbling of oxygen. After irradiation for 1 hour, the sensitizer was removed by filtration and the solution concentrated under reduced pressure. Purification by preparative TLC (methanol/dichloromethane, 20:80) gave the dioxetane 6, (0.0053 g, 0.0076 mmol, 46%). Analytical TLC spot showed yellow chemiluminescence upon heating.

$^1$H NMR (CDCl$_3$/CD$_3$OD, 3:1) δ: 0.88–1.98 (m, 12H), 2.32 (bs, 1H), 3.06 (bs, 1H), 3.65 (m, 4H), 6.53–8.34 (m, 13H).

Chemiluminescent Detection of Bovine Serum Albumin Directly Labeled with a Dioxetane.

1. Preparation of BSA-Dioxetane Conjugates

To a solution of BSA (0.15 g) in dioxane-borate buffer (dioxane/H$_2$O, 1:9) solution (pH 7.5) (10 mL), the dioxetane N-hydroxysuccinimide ester 1a was added with stirring. After stirring for 0.5 hours at room temperature, TLC (methanol/dichloromethane 10:90) showed trace amounts of unbound label. The solution was concentrated by ultrafiltration under high pressure. The reaction mixture was transferred into a 10 mL ultrafiltration cell (Amicon, YM30, 25 mm, >30,000 MW cutoff). The cell was capped and attached to a N$_2$ inlet. Filtration was effected initially by passing N$_2$ (20 psi) with gentle stirring. After approximately 5 minutes the N$_2$ pressure was gradually increased to 50 psi. The solution (dioxane/water) was collected into a beaker through the outlet. The concentrate was washed with aqueous dioxane (dioxane/H$_2$O, 5:95) (10 mL), followed by water (10 mL). The concentrate was lyophilized to give the conjugate as a white flaky solid.

To a solution of BSA (0.05 g) in dioxane-borate buffer (dioxane/H$_2$O, 1:9) solution (pH 7.6) (2.7 mL), the dioxetane N-hydroxysuccinimide ester 1b dissolved in dioxane (0.3 mL) was added with stirring. After stirring for 1 hour at room temperature, the solution was concentrated by ultrafiltration under pressure. The concentrate was washed with aqueous dioxane (dioxane/H$_2$O, 5:95) (5 mL) and distilled water (5 mL). The concentrate was lyophilized to give the conjugate as a white flaky solid.

To a solution of BSA (0.05 g) in dioxane-borate buffer (dioxane/H$_2$O, 1:9) solution (pH 7.6) (2.7 mL), the dioxetane N-hydroxysuccinimide ester 1c dissolved in dioxane (0.3 mL) was added with stirring. After stirring for 1 hour at room temperature, the solution was concentrated by ultrafiltration under pressure. The concentrate was washed with aqueous dioxane (dioxane/H$_2$O, 5:95) (5 mL) and distilled water (5 mL). The concentrate was lyophilized to give the conjugate as a white flaky solid.

2. Chemiluminescent Detection of BSA-Dioxetane Conjugates

Chemiluminescence measurements were conducted in single Dynatech Immulon wells placed in a light-tight holder. The luminescence was detected at the bottom of the well using a fiber optic connected to an Ortex photon-counter. Light intensity was measured with an RCA A-31034A gallium-arsenide PMT cooled to -78° C.

2.4 mg of the conjugate of BSA and dioxetane 1a described above was placed in a micro-titer well and 90 µL neutral CTAB (0.00125M) added so as to dissolve the white fluffy solid. A 10M NaOH solution (10 µL) was injected at about 25° to the above solution and the chemiluminescence generated recorded with a luminometer. The intensity of the luminescence as shown in FIG. 1 provides a direct measure of the labeled protein.

Figure 2:
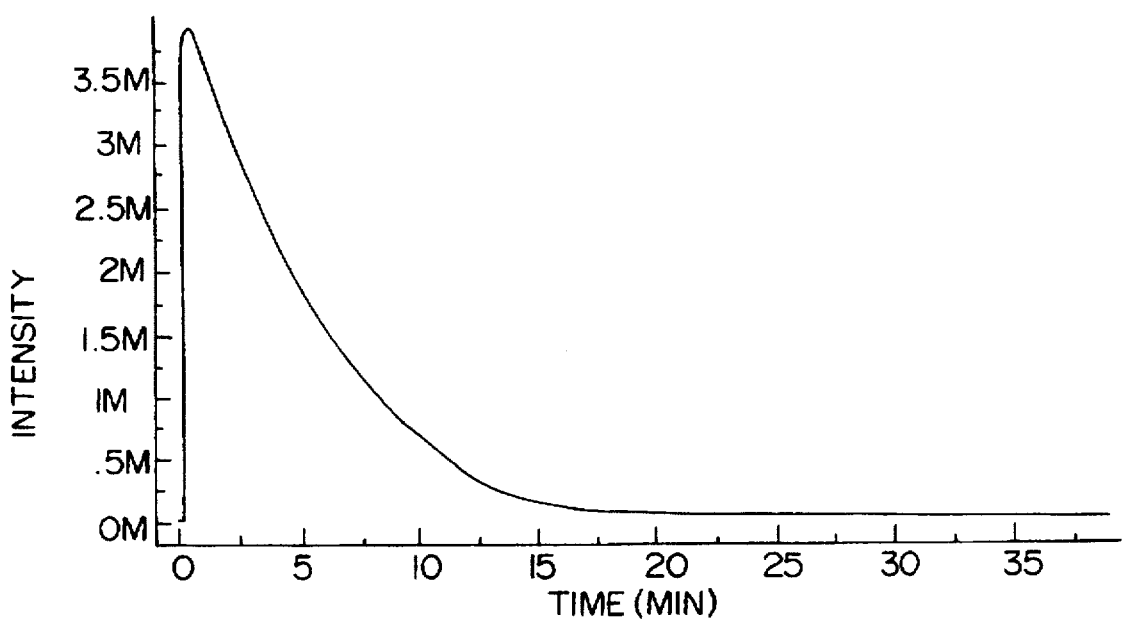
FIG. 2 is a graph of intensity versus time for the BSA labeled with dioxetane 1a described hereinafter in DMSO when triggered with tetrabutylammonium fluoride (TBAF).

For triggering in an organic media, 1.2 mg of the conjugate of BSA and dioxetane 1a was placed in a micro-titer well and DMSO (90 µL) added to it. A 0.1M tetrabutylammonium fluoride (TBAF) solution in DMSO (10 µL) was injected at about 25° C. to the above solution and the intensity of the luminescence recorded as shown in FIG. 2.

Chemiluminescent Detection of Antibodies Directly Labeled with a Dioxetane

1. Preparation of Dioxetane-linked Antibody

Figure 3:
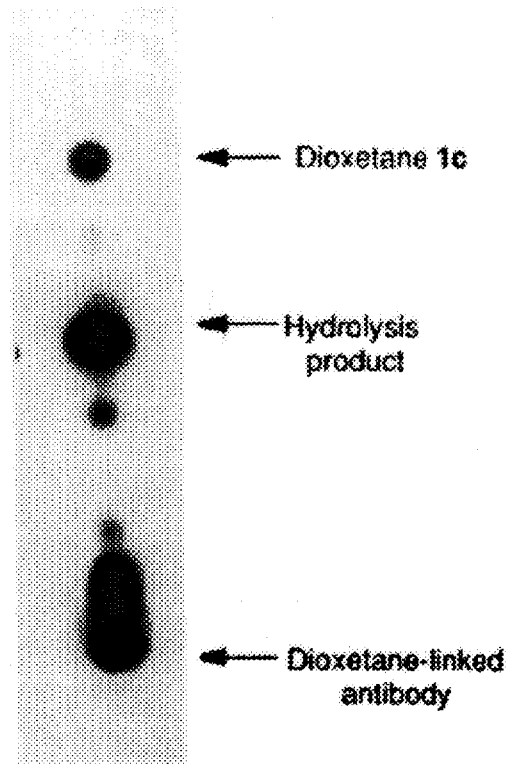
FIG. 3 shows an X-ray film exposed to TLC silica plate on which goat antimouse IgG labeled with dioxetane 1c has been chromatographed to separate non-labeled components and then triggered.

Dioxetane 1c (100 µg) in 125 µL of DMF was added slowly (over 10 seconds) to a vigorously vortexed solution (2 ml) of 25 mM Tris-HCl (pH 7.5), 1.4 mM CTAB, 1.4 mM CTAB containing 100 µg of goat antimouse IgG (Cappel, Cat. no. 0611-0231, Lot 32614). The solution was incubated at room temperature for 24 hours and then stored at 40° C. TLC analysis of the product on silica plates (methanol/CH$_2$Cl 8:92) indicated that the majority of the starting dioxetane had either become covalently linked to the antibody or the NHS functionality had been hydrolyzed. Shown in FIG. 3 is the exposure to X-ray film of the resulting TLC plate following triggering with a solution of tetrabutylammonium fluoride in anhydrous DMSO (20% w/v). In this TLC analysis the starting dioxetane 1c runs to the top of the plate and the dioxetane-linked antibody remains at the origin.

2. Purification of Dioxetane-linked Antibody

Figure 4:
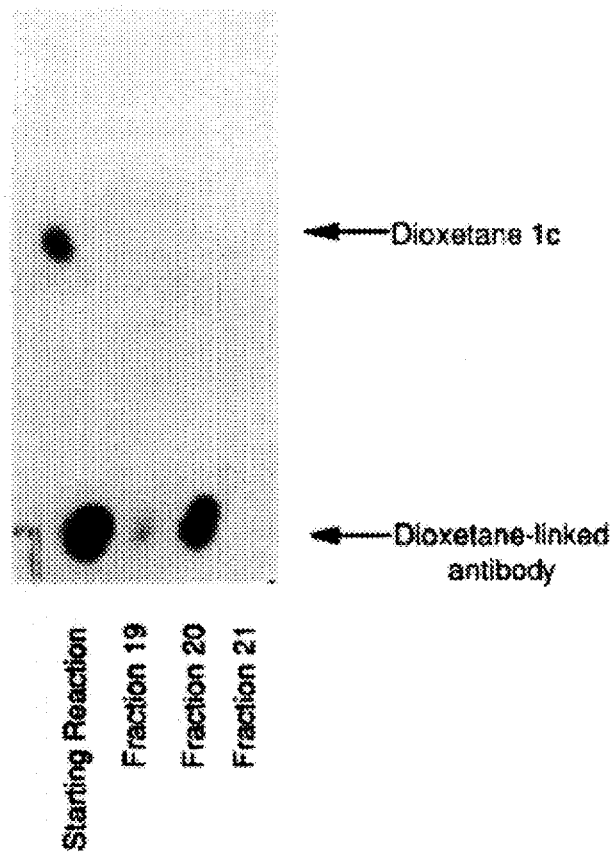
FIG. 4 shows an X-ray film exposed to a liquid chromatographically separated materials containing antimouse IgG which are triggered, wherein Fraction 20 contains the purified labeled antimouse IgG.

The labeled antibody was separated from non-linked dioxetane compounds by FPLC using a 30 cm Pharmacia Superose 12 column. An aliquot (850 µL) of the crude reaction was centrifuged for 10 minutes at 10,000 rpm in an Eppindorf microcentrifuge. It was then injected onto the column which had been equilibrated with a solution of 20 mM Tris-HCl pH 7.5, 0.15M NaCl, 1 mM CTAB. The dioxetane modified antibody was eluted with this same buffer at a flow rate of 0.12 mL/min. Fractions were checked by TLC on silica plates (methanol/CH$_2$CH$_2$ 8:92) to determine which contained the dioxetane-linked antibody. The TLC analysis of the fractions that contained the dioxetane-linked antibody (FIG. 4) (which used a triggering procedure as described for the TLC shown in FIG. 3) clearly shows that these fractions contain only this product and are free of starting material and hydrolysis product.

3. Western Blot Using Dioxetane-linked Antibody

Figure 5:
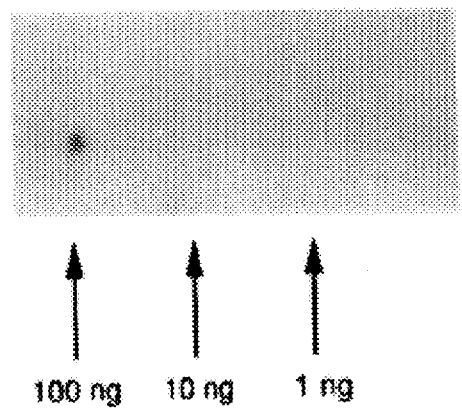
FIG. 5 shows a chemiluminescent Western dot blot wherein different concentrations of mouse IgG on a nylon membrane are contacted with the dioxetane labeled antimouse IgG.

Mouse IgG (Cappel) was spotted onto an MSI nylon membrane (20 cm×80 cm) and dried under vacuum for 30 minutes. The membrane was placed in a hybridization bag, 10 ml of a solution containing 0.1M Tris-HCl pH 7.5, 0.15M NaCl, 0.05% Tween 20 was added, the bag sealed and then incubated at 25° C. for one hour with gentle agitation. The bag was opened, the blocking solution drained and replaced with 10 ml of a solution containing 0.1M Tris-HCl pH 7.5, 0.15M NaCl, 0.05% Tween 20, 1% skim milk, and 200 µL of the pooled fractions from the FPLC purification of the above dioxetane-labeled antibody (approximately 5 µg modified IgG). The bag was sealed and the membrane was allowed to incubate overnight at room temperature. The membrane was then removed from the bag, rinsed under a stream of deionized water for one minute, and placed in a shallow dish containing 20 ml of a solution containing 0.1M Tris-HCl pH 7.5, 0.15M NaCl, 0.05% Tween 20, 0.1% SDS. The dish was gently rocked for 15 minutes, the solution drained and the wash repeated twice. The membrane was rinsed under a stream of deionized water for one minute and then dried under vacuum. The membrane was exposed by placing it on a thin glass over a sheet of Kodak XAR5 X-ray film and triggering by the addition of 20% (w/v) tetrabutylammonium fluoride in anhydrous DMSO. Hybridization of the modified antibody was observed to the spotted sample containing 100 ng of protein (FIG. 5). These results demonstrate that detection of dioxetane-labeled biomolecules by chemiluminescence is obtained.

We claim:

1. An alkene compound of the formula shown below used to produce a 1,2-dioxetane compound:

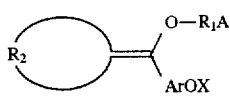

wherein Ar is an aromatic substituent selected from the group consisting of phenyl and naphthyl, wherein A is a substituent which couples with an organic or biological molecule to provide the dioxetane compound as a label on the molecule and wherein A is selected from the group consisting of hydroxyl, amino, halogen, cyano, carboxylic acid, $NH(CH_2)_mOH$ where m is 2 to 20, succinimidoxy, biotin and carboxyfluorescein substituents, wherein $R_1$ is a linking substituent selected from the group consisting of a —(CH2)$_n$ group, a —(CH2)$_n$NH— group and a —(CH$_2$)$_n$CO— group, where n is an integer between about 1 and 30, wherein X is a chemically labile substituent which is removed by an activating agent other than an enzyme so that light is produced by the 1,2-dioxetane and $R_2$ C is a polycyclic alkylene substituent containing 6 to 30 carbon atoms.

2. The compound of claim 1 wherein

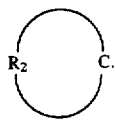

is adamantyl.

3. The compound of claim 1 wherein OX is selected from the group consisting of hydroxyl, alkyl ester, aryl ester, alkyl siloxy and aryl siloxy.

4. An alkene compound of the following formula used to produce a 1,2-dioxetane compound:

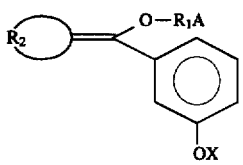

wherein A is a substituent which couples with an organic or biological molecule to provide the dioxetane compound as a label on the molecule and is selected from the group consisting of hydroxyl, amino, halogen, cyano, carboxylic acid, $NH(CH_2)_mOH$ where m is 2 to 20, succinimidoxy, biotin and carboxyfluorescein substituents, wherein $R_1$ is a linking substituent selected from the group consisting of a—(CH2)n—group, a —(CH2)$_n$NH— group and a —(CH2)$_n$CO— group, where n is an integer between about 1 and 30, wherein X is a chemically labile substituent which is removed by an activating agent other than an enzyme so that light is produced by the 1,2-dioxetane and $R_2$ C is a polycyclic alkylene substituent containing 6 to 30 carbon atoms.

5. The compound of claim 4 wherein

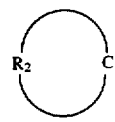

is adamantyl.

6. The compound of claim 4 wherein OX is selected from the group consisting of hydroxyl, alkyl ester, aryl ester, alkyl siloxy and aryl siloxy.

7. The compound of claim 4 wherein A couples with substituents in the organic or biological molecule selected from the group consisting of amine, thiol and carboxylic acid substituents.

8. An alkene compound of the following formula used to produce a 1,2-dioxetane compound:

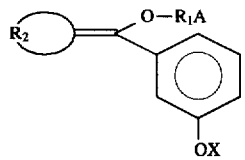

wherein $R_1$ is

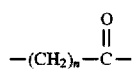

n is an integer between 1 and 30, A is selected from the group consisting of hydroxyl, $NH(CH_2)_m$)OH where m is 2 to 20 and succinimidoxy substituents, X is a chemically labile group which is removed by an activating agent other than an enzyme so that light is produced by the 1,2-dioxetane, and wherein $R_2$ C is a polycyclic alkylene group containing 6 to 30 carbon atoms.

9. The alkene compound of claim 8 wherein A is the succinimidoxy substituent and $R_2$ C— is an adamantyl substituent and having the formula

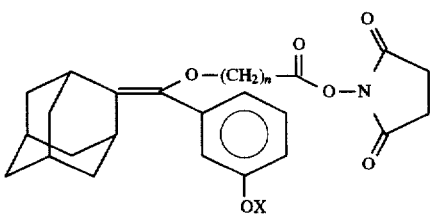

10. The alkene compound of claim 9 wherein n is 3 and X is H and having the formula:

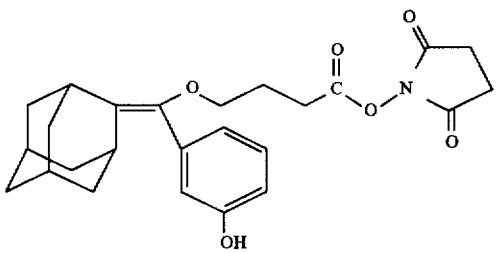

11. The alkene compound of claim 9 wherein n is 3 and OX is silyloxy of the formula:

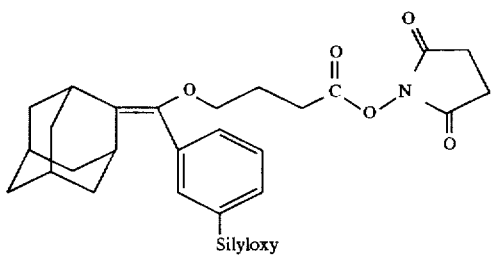

Silyloxy wherein silyloxy is selected from the group consisting of a tertbutyldimethylsilyloxy and tertbutyldiphenylsilyloxy groups.

12. The alkene compound of claim 4 wherein $R_1$ is the —$(CH_2)_n$NH— group, wherein n is 2, $R_2$ C— is an adamantyl substituent and A is a biotin containing substituent and having the formula

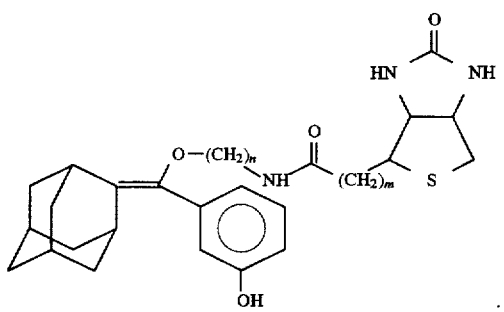

13. The alkene of claim 8 wherein

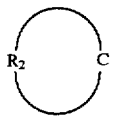

is an adamantyl group and A is $NH(CH_2)_m$ OH.

14. The alkene of claim 13 wherein n is 3 and m is 6 and OX is selected from the group consisting of tertbutyldimethylsilyloxy and tertbutyldiphenylsilyloxy.

15. The alkene of claim 4 wherein

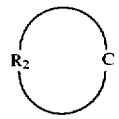

is an adamantyl group, $R_1$ is $(CH_2)_n$ where n is an integer between 1 and 30 and wherein OX is selected from hydroxy, tertbutyldimethylsilyloxy and tertbutyldiphenylsilyloxy.

16. The alkene of claim 15 wherein A is selected from the group consisting of carboxylic acid, hydroxyl and primary amino groups.

17. The alkene of claim 16 wherein n is 2.

18. The alkene of claim 16 wherein n is 3.

19. The alkene of claim 4 wherein $R_1$ is the —$(CH_2)_n$— group, n is 2, $R_2$ C is an adamantyl substituent, A is the carboxyfluorescein substituent and having the formula

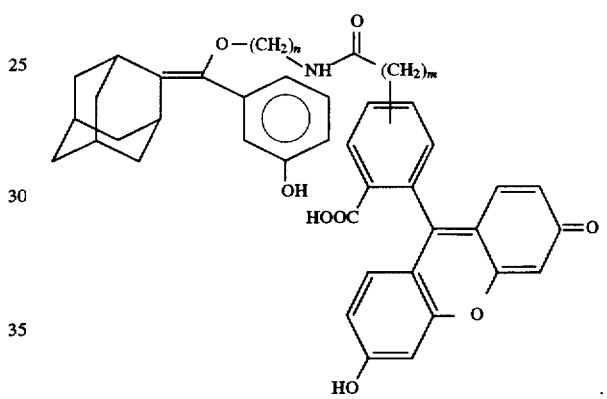

* * * * *

UNITED STATES PATENT AND TRADEMARK OFFICE
CERTIFICATE OF CORRECTION

PATENT NO. : 5,795,987
DATED : August 18, 1998
INVENTOR(S) : Arthur P. Schaap, Louis J. Romano, Jaidev S. Goudar It is certified that error appears in the above—identified patent and that said Letters Patent is hereby corrected as shown below:

Column 3, line 62, "(1897)" should be -- (1987)--.

Column 8, line 40 (Table 1), "  " should be --  --.

Column 8, line 43 (Table 1), "  " should be --  --.

Column 11, line 5, "$R_2C$-" should be --  --.

Column 11, line 33, "$R_2C$-" should be --  --.

Column 11, line 37, "$R_2C$-" should be --  --.

Column 13, lines 35-40, " 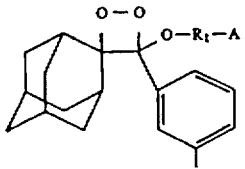 "

should be -- 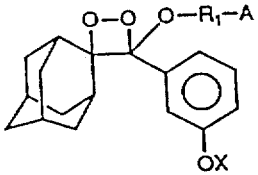 --.

Column 22, line 28, "(2-15 mL)" should be --(2X15 mL)--.

UNITED STATES PATENT AND TRADEMARK OFFICE
CERTIFICATE OF CORRECTION

PATENT NO. : 5,795,987
DATED : August 18, 1998
INVENTOR(S) : Arthur P. Schaap, Louis J. Romano, Jaidev S. Goudar It is certified that error appears in the above—identified patent and that said Letters Patent is hereby corrected as shown below:

Column 24, line 46, "methyleneadamantane" should be --methylene]adamantane--.

Column 25, lines 30-31, "129,03" should be --129.03--.

Column 26, line 28, "alkane 19" should be --alkene 19--.

Column 29, line 37, "In dust" should be --Zn dust--.

Column 29, line 52, "CDCl$_3$)6" should be --(CDCl$_3$) δ --.

Column 29, line 55, "CDCl$_3$)6" should be --(CDCl$_3$) δ --.

Column 33, line 1, "prescence" should be --presence--.

Column 38, line 11, "at 40°C" should be --at 4°C--.

Column 39, line 19 (Claim 1), "R$_2$C" should be --$\widehat{R_2C}$--.

Column 39, line 54 (Claim 4), "R$_2$C" should be --$\widehat{R_2C}$--.

Column 40, line 32 (Claim 8), "R$_2$C" should be --$\widehat{R_2C}$--.

Column 40, line 36 (Claim 9), "R$_2$C" should be --$\widehat{R_2C}$--.

UNITED STATES PATENT AND TRADEMARK OFFICE
CERTIFICATE OF CORRECTION

PATENT NO. : 5,795,987
DATED : August 18, 1998
INVENTOR(S) : Arthur P. Schaap, Louis J. Romano, Jaidev S. Goudar It is certified that error appears in the above—identified patent and that said Letters Patent is hereby corrected as shown below:

Column 41, line 16 (Claim 12), "$R_2C$" should be --$\overset{\frown}{R_2\underset{\smile}{C}}$--.

Column 42, line 21 (Claim 19), "$R_2C$" should be --$\overset{\frown}{R_2\underset{\smile}{C}}$--.

Signed and Sealed this

Twenty-third Day of March, 1999

Q. TODD DICKINSON

Attest:

Attesting Officer

Acting Commissioner of Patents and Trademarks